US009376698B2

(12) United States Patent
Zheng et al.

(10) Patent No.: US 9,376,698 B2
(45) Date of Patent: Jun. 28, 2016

(54) MUTANT DNA POLYMERASES

(75) Inventors: Weidong Zheng, Carlsbad, CA (US); Jun E. Lee, San Diego, CA (US); Robert Jason Potter, San Marcos, CA (US); David Mandelman, Carlsbad, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 569 days.

(21) Appl. No.: 12/052,682

(22) Filed: Mar. 20, 2008

(65) Prior Publication Data

US 2008/0254525 A1    Oct. 16, 2008

Related U.S. Application Data

(62) Division of application No. 11/170,762, filed on Jun. 28, 2005, now abandoned.

(51) Int. Cl.
*C12N 9/12* (2006.01)
*C12P 19/34* (2006.01)
*C12Q 1/68* (2006.01)

(52) U.S. Cl.
CPC .............. *C12P 19/34* (2013.01); *C12N 9/1252* (2013.01); *C12N 9/1276* (2013.01); *C12Q 1/686* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,795,699 | A | 1/1989 | Tabor et al. |
| 4,889,818 | A | 12/1989 | Gelfand et al. |
| 4,962,020 | A | 10/1990 | Tabor et al. |
| 4,965,188 | A | 10/1990 | Mullis et al. |
| 5,047,342 | A | 9/1991 | Chatterjee |
| 5,079,352 | A | 1/1992 | Gelfand et al. |
| 5,173,411 | A | 12/1992 | Tabor et al. |
| 5,210,015 | A | 5/1993 | Gelfand et al. |
| 5,244,797 | A | 9/1993 | Kotewicz et al. |
| 5,270,179 | A | 12/1993 | Chatterjee |
| 5,405,776 | A | 4/1995 | Kotewicz et al. |
| 5,436,149 | A | 7/1995 | Barnes |
| 5,487,972 | A | 1/1996 | Gelfand et al. |
| 5,498,523 | A | 3/1996 | Tabor et al. |
| 5,512,462 | A | 4/1996 | Cheng |
| 5,614,365 | A | 3/1997 | Tabor et al. |
| 5,789,166 | A | 8/1998 | Bauer et al. |
| 5,804,375 | A | 9/1998 | Gelfand |
| 5,939,292 | A | 8/1999 | Gelfand et al. |
| 5,994,056 | A | 11/1999 | Higuchi |
| 5,994,076 | A | 11/1999 | Chenchik |
| 6,130,364 | A | 10/2000 | Jakobovits et al. |
| 6,228,628 | B1 * | 5/2001 | Gelfand et al. ............. 435/194 |
| 6,569,627 | B2 | 5/2003 | Wittwer |
| 6,875,573 | B2 * | 4/2005 | Fuller et al. ............... 435/91.2 |
| 2003/0113972 | A1 | 6/2003 | Hayashi |
| 2004/0197800 | A1 | 10/2004 | Borns |
| 2006/0292578 | A1 | 12/2006 | Zheng et al. |
| 2007/0020622 | A1 | 1/2007 | Lee et al. |

FOREIGN PATENT DOCUMENTS

| | | |
|---|---|---|
| EP | 1904518 | 10/2010 |
| EP | 2314596 | 6/2013 |
| WO | 92/06188 | 4/1992 |
| WO | 92/06200 | 4/1992 |
| WO | 94/26766 | 11/1994 |
| WO | 96/10640 | 4/1996 |
| WO | 97/09451 | 3/1997 |
| WO | 98/06736 | 2/1998 |
| WO | 99/10366 | 8/1998 |
| WO | 03/025132 | 4/2003 |
| WO | 03/066804 | 8/2003 |
| WO | 2007/002031 | 1/2007 |

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
EP 06799952.4; Supplementary European Search Report mailed Jan. 29, 2009, 9 pages.
EP 10174796.2; Extended European Search Report mailed Jun. 6, 2011, 12 pages.
EP 10174796.2; Partial European Search Report mailed Mar. 14, 2011, 8 pages.
PCT/US2006/023899; International Search Report and Written Opinion mailed May 26, 2007, 14 pages.
PCT/US2006/023899; International Preliminary Report on Patentability mailed Jan. 17, 2008, 9 pages.
Ando, T. et al., "A One-Tube Method of Reverse Transcription-PCR to efficiently Amplify a 3-kilobase Region From the RNA Polymerase Gene to the Poly(A) Tail of small Round-structured Viruses(Norwalk-Like Viruses)", *J. Clin. Microbiol.*, vol. 35, American Society for Microbiology, Mar. 1997, 570-577.
Barnes, et al., "PCR Amplification of Up to 35-kb DNA With High Fidelity and High Yield From λ Bacteriophage Templates," *Proc. Natl. Acad. Sci. USA.*, vol. 91, No. 6, 1994, 2216-2220.
Barnes, "The Fidelity of Taq Polymerase Catalyzing PCR is Improved by an N-Terminal Deletion", *Gene*, vol. 112, No. 1, Mar. 1, 1992, 29-35.
Cenatiempo, Y., "Prokaryotic gene expression in vitro: transcription-translation coupled systems", *Biochimie*, vol. 68, Elsevier, 1986, 505-515.
Choi, J. et al., "Purification and characterization of the 5' fwdarw 3' exonuclease domain-deleted Thermus filiformis DNA polymerase expressed in *Escherichia coli*," *Biotechnology Letters*, vol. 23, No. 20, Oct. 2001, 1647-1652.
Cline, Janice et al., "PCR Fidelity of Pfu DNA Polymerase and Other Thermostable DNA Polymerases", *Nucleic Acids Research*, vol. 24, No. 18, Oxford University Press, Sep. 1996, 3546-3551.
Darzins, A. et al., "Cloning of genes controlling alginate biosynthesis from a mucoid cystic fibrosis isolate of Pseudomonas aeruginosa", *Journal of Bacteriology*, vol. 159, No. 1, Jul. 1984, 9-18.
Flaman, Jean-Michele et al., "A Rapid PCR Fidelity Assay", *Nucleic Acids Research*, vol. 22, No. 15, Oxford University Press, Aug. 11, 1994, 3259-3260.

(Continued)

*Primary Examiner* — Richard Hutson

(57) ABSTRACT

An isolated mutant Tfi DNA polymerase having a D144A point mutation. This polymerase may be used in methods including, but not limited to, nucleic acid synthesis, DNA sequencing, nucleic acid amplification and cDNA synthesis.

12 Claims, 5 Drawing Sheets

(56) References Cited

OTHER PUBLICATIONS

Fremont, P S. et al., "A Domain of the Klenow Fragment of *Escherichia coli* DNA Polymerase I Has Polymerase but No Exonuclease Activity", *Proteins: Structure, Function, and Genetics*, vol. 1, 1986, 66-73.

Glick, Bernard R. et al., "Factors affecting the expression of foreign proteins in *Escherichia coli*", *Journal Industrial Microbiology*, vol. 1, Elsevier Science Publishers, 1987, 277-282.

Glyczan, Thomas, "Molecular Cloning in Bacillus subtilis", *The Molecular Biology of the Bacilli*, Academic Press, 1982, 307-329.

Gold, L. et al., "Translational Initiation in Prokaryotes", *Ann. Rev. Microbiol.*, vol. 35, Annual Reviews, Inc., 1981, 365-403.

Gottesman, Susan et al., "Bacterial Regulation: Global Regulatory Networks", *Ann. Rev. Genet.*, vol. 18, Annual Reviews, Inc., 1984, 415-441.

Gutman, Pablo D. et al., "Conserved sites in the 5'-3' exonuclease domain of *Escherichia coli* DNA polymerase", *Nucleic Acids Research*, vol. 21, No. 18, 1993, 4406-4407.

John, Joseph F. et al., "Plasmids as Epidemiologic Markers in Nosocomial Gram-Negative Bacilli: Experience at a University and Review of the Literature", *Reviews of Infectious Diseases*, vol. 8, No. 5, The University of Chicago, Sep. 1986, 693-704.

Joyce, Catherine M., "Can DNA polymerase I (Klenow Fragment) serve as a model for other polymerases?", *Current Opinion in Structural Biology*, vol. 1, 1991, 123-129.

Joyce, Catherine M. et al., "Nucleotide Sequence of the *Escherichia coli* polA Gene and Primary Structure of DNA Polymerase", *The Journal of Biological Chemistry*, vol. 257, No. 4, Feb. 25, 1982, 1958-1964.

Kendall, Kevin J. et al., "Plasmid Transfer in Streptomyces lividans: Identification of a kil-kor System Associated with the Transfer Region of pIJ101", *Journal of Bacteriology*, vol. 169, No. 9, American Society for Microbiology, Sep. 1987, 4177-4183.

Ollis, D.L. et al., "Structure of large fragment of *Escherichia coli* DNA polymerase I complexed with dTMP", *Nature*, vol. 313, Feb. 28, 1985, 762-766.

Sambrook, et al., "Ch: 16.30-16.60-Introduction of Recombinant Vectors into Mammalian Cells", *Molecular Cloning, a Laboratory Manual*, 2nd ed., Cold Spring Harbor Laboratory Press, Cold Spring Harbor, NY, 1989, 16.30-16.60.

Sanger, G et al., "Rapid filter assay for the detection of DNA polymerase activity: direct identification of the gene for the DNA polymerase for Thermus aquaticus", *Gene*, vol. 97, Elsevier, 1991, 119-123.

Ulmanen, I et al., "Transcription and Translation of Foreign Genes in Bacillus subtilis by the Aid of a Secretion Vector", *Journal of Bacteriology*, vol. 162, No. 1, American Society for Microbiology, Apr. 1985, 176-182.

Ward, Judith M. et al., "Construction and characterisation of a series of multi-copy promoter-probe plasmid vectors for Streptomyces using the aminoglycoside phosphotransferase gene from Tn5 as indicator", *Mol. Gen. Genet.*, vol. 203, 1986, 468-478.

\* cited by examiner

FIG. 4A

Met Arg Gly Met Leu Pro Leu Phe Glu Pro Lys Gly Arg Val Leu Leu

Val Asp Gly His His Leu Ala Tyr Arg Thr Phe His Ala Leu Lys Gly

Leu Thr Thr Ser Arg Gly Glu Pro Val Gln Ala Val Tyr Gly Phe Ala

Lys Ser Leu Leu Lys Ala Leu Lys Glu Asp Gly Asp Ala Val Ile Val

Val Phe Asp Ala Lys Ala Pro Ser Phe Arg His Glu Ala Tyr Gly Gly

Tyr Lys Ala Gly Arg Ala Pro Thr Pro Glu Asp Phe Pro Arg Gln Leu

Ala Leu Ile Lys Glu Leu Val Asp Leu Leu Gly Leu Ala Arg Leu Glu

Val Pro Gly Tyr Glu Ala Asp Asp Val Leu Ala Ser Leu Ala Lys Lys

Ala Glu Lys Glu Gly Tyr Glu Val Arg Ile Leu Thr Ala Asp Lys Asp

Leu Tyr Gln Leu Leu Ser Asp Arg Ile His Val Leu His Pro Glu Gly

Tyr Leu Ile Thr Pro Ala Trp Leu Trp Glu Lys Tyr Gly Leu Arg Pro

Asp Gln Trp Ala Asp Tyr Arg Ala Leu Thr Gly Asp Glu Ser Asp Asn

Leu Pro Gly Val Lys Gly Ile Gly Glu Lys Thr Ala Arg Lys Leu Leu

Glu Glu Trp Gly Ser Leu Glu Ala Leu Leu Lys Asn Leu Asp Arg Leu

Lys Pro Ala Ile Arg Glu Lys Ile Leu Ala His Met Asp Asp Leu Lys

Leu Ser Trp Asp Leu Ala Lys Val Arg Thr Asp Leu Pro Leu Glu Val

Asp Phe Ala Lys Arg Arg Glu Pro Asp Arg Glu Arg Leu Arg Ala Phe

Leu Glu Arg Leu Glu Phe Gly Ser Leu Leu His Glu Phe Gly Leu Leu

Glu Ser Pro Lys Ala Leu Glu Glu Ala Pro Trp Pro Pro Pro Glu Gly

Ala Phe Val Gly Phe Val Leu Ser Arg Lys Glu Pro Met Trp Ala Asp

Leu Leu Ala Leu Ala Ala Ala Arg Gly Gly Arg Val His Arg Ala Pro

Glu Pro Tyr Lys Ala Leu Arg Asp Leu Lys Glu Ala Arg Gly Leu Leu

Ala Lys Asp Leu Ser Val Leu Ala Leu Arg Glu Gly Leu Gly Leu Pro

Pro Gly Asp Asp Pro Met Leu Leu Ala Tyr Leu Leu Asp Pro Ser Asn

Thr Thr Pro Glu Gly Val Ala Arg Arg Tyr Gly Gly Glu Trp Thr Glu

Glu Ala Gly Glu Arg Ala Ala Leu Ser Glu Arg Leu Phe Ala Asn Leu

Trp Gly Arg Leu Glu Gly Glu Glu Arg Leu Leu Trp Leu Tyr Arg Glu

Val Glu Arg Pro Leu Ser Ala Val Leu Ala His Met Glu Ala Thr Gly

FIG. 4B

Val Arg Leu Asp Val Ala Tyr Leu Arg Ala Leu Ser Leu Glu Val Ala
Glu Glu Ile Ala Arg Leu Glu Ala Glu Val Phe Arg Leu Ala Gly His
Pro Phe Asn Leu Asn Ser Arg Asp Gln Leu Glu Arg Val Leu Phe Asp
Glu Leu Gly Leu Pro Ala Ile Gly Lys Thr Glu Lys Thr Gly Lys Arg
Ser Thr Ser Ala Ala Val Leu Glu Ala Leu Arg Glu Ala His Pro Ile
Val Glu Lys Ile Leu Gln Tyr Arg Glu Leu Thr Lys Leu Lys Ser Thr
Tyr Ile Asp Pro Leu Pro Asp Leu Ile His Pro Arg Thr Gly Arg Leu
His Thr Arg Phe Asn Gln Thr Ala Thr Ala Thr Gly Arg Leu Ser Ser
Ser Asp Pro Asn Leu Gln Asn Ile Pro Val Arg Thr Pro Leu Gly Gln
Arg Ile Arg Arg Ala Phe Ile Ala Glu Glu Gly Trp Leu Leu Val Ala
Leu Asp Tyr Ser Gln Ile Glu Leu Arg Val Leu Ala His Leu Ser Gly
Asp Glu Asn Leu Ile Arg Val Phe Gln Glu Gly Arg Asp Ile His Thr
Glu Thr Ala Ser Trp Met Phe Gly Val Pro Arg Glu Ala Val Asp Pro
Leu Met Arg Arg Ala Ala Lys Thr Ile Asn Phe Gly Val Leu Tyr Gly
Met Ser Ala His Arg Leu Ser Gln Glu Leu Ala Ile Pro Tyr Glu Glu
Ala Gln Ala Phe Ile Glu Arg Tyr Phe Gln Ser Phe Pro Lys Val Arg
Ala Trp Ile Glu Lys Thr Leu Glu Glu Gly Arg Arg Arg Gly Tyr Val
Glu Thr Leu Phe Gly Arg Arg Arg Tyr Val Pro Asp Leu Glu Ala Arg
Val Lys Ser Val Arg Glu Ala Ala Glu Arg Met Ala Phe Asn Met Pro
Val Gln Gly Thr Ala Ala Asp Leu Met Lys Leu Ala Met Val Lys Leu
Phe Pro Arg Leu Glu Glu Met Gly Ala Arg Met Leu Leu Gln Val His
Asp Glu Leu Val Leu Glu Ala Pro Lys Glu Arg Ala Glu Ala Val Ala
Arg Leu Ala Lys Glu Val Met Glu Gly Val Tyr Pro Leu Ala Val Pro
Leu Glu Val Glu Val Gly Ile Gly Glu Asp Trp Leu Ser Ala Lys Glu (SEQ ID NO.: 10)

MUTANT DNA POLYMERASES

CROSS REFERENCE TO RELATED APPLICATIONS

This application is a divisional of U.S. application Ser. No. 11/170,762, filed Jun. 28, 2005, which is incorporated herein by reference in its entirety.

FIELD OF THE INVENTION

The present invention relates DNA polymerase blends and mutant DNA polymerases. More specifically, the invention relates to a combination of DNA polymerases which have, and which are substantially reduced in, 5-exonuclease activity.

SEQUENCE LISTING

The instant application contains a Sequence Listing which has been submitted electronically in ASCII format and is hereby incorporated by reference in its entirety. Said ASCII copy, created on Jul. 2, 2014, is named IVGN270.1DIV_SL.txt and is 19,818 bytes in size.

BACKGROUND OF THE INVENTION

DNA polymerases synthesize formation of DNA molecules that are complementary to all or a portion of a nucleic acid template. Upon hybridization of a primer to the single-stranded template, polymerases synthesize DNA in the 5' to 3' direction, i.e., successively adding nucleotides to the 3'-hydroxyl group of the growing strand. Thus, for example, in the presence of deoxynucleoside triphosphates (dNTPs) and a primer, a new DNA molecule, complementary to the single stranded nucleic acid template, can be synthesized. Typically an RNA or DNA template is used for synthesizing a complementary DNA molecule. However, other templates, such as chimeric templates or modified nucleic acid templates are also usable for synthesizing complementary molecules of polymerized nucleic acids. A DNA-dependent DNA polymerase utilizes a DNA template and produces a DNA molecule complementary to at least a portion of the template. An RNA-dependent DNA polymerase, i.e. a reverse transcriptase, utilizes an RNA template to produce a DNA strand complementary to at least a portion of the template, i.e., a cDNA. A common application of reverse transcriptase has been to transcribe mRNA into cDNA. Some DNA polymerases have both DNA-dependent DNA polymerase activity and RNA-dependent DNA polymerase activity.

In addition to a polymerase activity, DNA polymerases may possess one or more additional catalytic activities. Typically, DNA polymerases may have a 3'-5' exonuclease ("proofreading") and a 5'-3' exonuclease activity. Each of these activities has been localized to a particular region or domain of the protein. For example, when *E. coli* polymerase I (pol I) is cleaved into two fragments by subtilisin, the larger ("Klenow") fragment has 3'-5' exonuclease and DNA polymerase activities and the smaller fragment has 5'-3' exonuclease activity.

DNA polymerases have been isolated from a variety of mesophilic and thermophilic organisms. DNA polymerases from thermophilic organisms typically have a higher optimum temperature for polymerization activity than enzymes isolated from mesophilic organisms. Thermostable DNA polymerases have been discovered in a number of thermophilic bacterial species, including, but not limited to, *Thermus aquaticus* (Taq), *Thermus filiformis* (Tfi), *Thermus thermophilus* (Tth), and species of the *Bacillus, Thermococcus, Sulfolobus* and *Pyrococcus* genera. In addition, thermostable DNA polymerases from a variety of other thermophiles are described in PCT WO 03/025132, the entire contents of which are incorporated herein by reference. Thermostable DNA polymerases have been exploited in numerous applications, including the polymerase chain reaction (PCR).

PCR is used to amplify a target nucleic acid by denaturation of the target DNA, hybridization of oligonucleotide primers to specific sequences on opposite strands of the target DNA molecule, and subsequent extension of these primers with a DNA polymerase, usually a thermostable DNA polymerase, to generate two new strands of DNA which then serve as templates for a further round of hybridization and extension. If the polymerase is thermostable, then there is no need to add fresh polymerase after every denaturation step since heat will not have destroyed the polymerase activity. In RT-PCR, a DNA primer is hybridized to a strand of the target RNA molecule, and subsequent extension of this primer with a reverse transcriptase generates a new strand of DNA (i.e., cDNA), which can serve as a template for PCR.

Thermostable DNA polymerases from *Thermus aquaticus* (Taq) made PCR feasible. Other thermostable polymerases having different properties (e.g., higher or lower fidelity; additional, enhanced, fewer or reduced catalytic activities; altered substrate use or preference; or different cofactor requirements) suitable for particular applications have been isolated from other organisms and/or made using recombinant DNA techniques.

SUMMARY OF THE INVENTION

One embodiment of the present invention is an isolated recombinant nucleic acid molecule encoding a *Thermus filiformis* (Tfi) DNA polymerase having a D144A point mutation, wherein said point mutation substantially reduces the 5'-exonuclease activity of said polymerase. The isolated nucleic acid molecule may further comprise an E437D point mutation. In one aspect of this embodiment, the mutant Tfi DNA polymerase is produced from one of the nucleic acid molecules described above.

In another embodiment, there is provided an isolated mutant Tfi DNA polymerase having a D144A point mutation. The present invention also provides an isolated mutant Tfi DNA polymerase having D144A and E437D point mutations. Another embodiment is a composition comprising at least two thermostable DNA polymerases wherein at least one of the polymerases is substantially reduced in 5' exonuclease activity (exo−) and wherein at least one of the polymerases has 5' exonuclease activity (exo+). The polymerases may be from the same species of thermophilic bacteria. The composition may further comprise at least two of the following components: detergent, buffer salt, deoxynucleoside triphosphate (DNTP) and dideoxynucleoside triphosphate (dNTP). In another embodiment, the composition comprises a detergent, buffer salt and DNTP. In one aspect, the 5'-exo− and 5'-exo+ polymerases are combined in a ratio of between 9:1 and 1:9 (exo−:exo+). In one embodiment, the ratio is 7:3 (exo−:exo+). The present invention also provides a vector comprising any of the isolated nucleic acid molecules described above, as well as a host cell comprising the vector. The nucleic acid molecule may be operably linked to a promoter.

The present invention also provides a method of synthesizing a double-stranded DNA molecule, comprising hybridizing a primer to a first DNA molecule; and incubating the DNA molecule in the presence of one or more deoxy- or dideoxyribonucleoside triphosphates and any of the DNA polymerases/compositions described above under conditions sufficient to synthesize a second DNA molecule complementary to all or a portion of the first DNA molecule.

Another embodiment is a method of amplifying a double stranded DNA molecule, comprising providing a first and second primer wherein the first primer is complementary to a sequence at or near the 3'-terminus of the first strand of the DNA molecule and the second primer is complementary to a sequence at or near the 3'-terminus of the second strand of the DNA molecule; hybridizing the first primer to the first strand and the second primer to the second strand in the presence of any of the DNA polymerases/compositions described above, under conditions such that the third strand complementary to the first strand and a fourth strand complementary to the second strand are synthesized; denaturing the first and third strands and the second and fourth strands; and repeating these steps one or more times.

There is also provided a kit for sequencing a DNA molecule, comprising a first container comprising any of the DNA polymerases/compositions described above; a second container comprising one or more dideoxyribonucleoside triphosphates; and a third container comprising one or more deoxyribonucleoside triphosphates.

The present invention also provides a kit for amplifying a DNA molecule, comprising a first container comprising any of the DNA polymerases/compositions described above; and a second container comprising one or more deoxyribonucleoside triphosphates.

Another embodiment is a method of preparing cDNA from mRNA, comprising contacting mRNA with an oligo(dT) primer or other complementary primer to form a hybrid; and contacting the hybrid with any of the DNA polymerases/ compositions described above and dATP, dCTP, dGTP and dTTP, whereby a cDNA-RNA hybrid is obtained.

The present invention also provides a method of preparing dsDNA from mRNA, comprising contacting mRNA with an oligo(dT) primer or other complementary primer to form a hybrid; and contacting the hybrid with any of the DNA polymerases/compositions described above, dATP, dCTP, dGTP, and dTTP, and an oligonucleotide or primer which is complementary to the a first strand cDNA, whereby dsDNA is obtained.

BRIEF DESCRIPTION OF THE DRAWINGS

FIGS. 4 (A and B) illustrates the amino acid sequence of Taq polymerase (SEQ ID NO: 10).

DETAILED DESCRIPTION OF THE INVENTION

Figure 1:
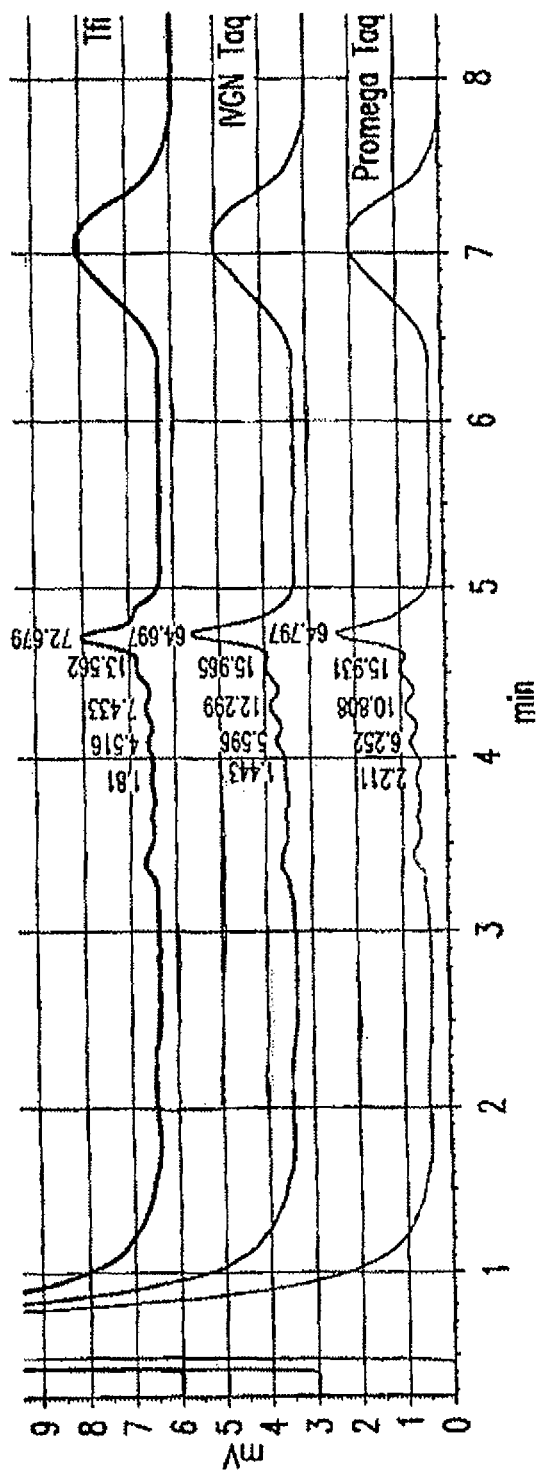
FIG. 1 is a representative chromatogram showing BRCA exon 11 437 bp amplification products using three DNA polymerases: Tfi exo-/exo+ blend (7:3 ratio) (top line); Taq (Invitrogen) (middle line); and Taq (Promega) (bottom line). The percentage of each peak is shown. The major peak is the homoduplex peak which shows the presence of PCR induced errors.

The present invention relates to thermostable DNA polymerase blends, and mutant DNA polymerases, which are substantially reduced in 5'-exonuclease activity. These polymerase blends and polymerases modulate 5'-exonuclease activity to enhance PCR performance. As used herein, the term "blend" refers to at least two DNA polymerases, at least one of which is substantially reduced in 5'-exonuclease activity (referred to herein as "exo-"), and at least one of which has 5'-exonuclease activity (referred to herein as "exo+"). The exo- and exo+ polymerases may be the same or different. For example, the blend may be an exo- Tfi polymerase combined with an exo+ Tfi polymerase, or may be an exo- Tfi polymerase combined with an exo+ Taq DNA polymerase. Tfi has about 78% identity and 86% similarity at the amino acid level compared to Taq. Both Tfi and Taq DNA polymerase have 5' to 3' exonuclease and 5' to 3' polymerase activities, yet lack 3' to 5' exonuclease activity. The exo- polymerases in the exo-/ exo+ blends are substantially reduced in 5'-exonuclease activity. In addition to exo+/exo- blends, also described are thermostable exo- DNA polymerases, which are reduced or substantially reduced in 5'-exo activity, particularly Tfi polymerases. Compositions, reaction mixtures, and kits containing such DNA polymerase blends, and exo- DNA polymerases, are also described herein, as are methods for nucleic acid synthesis, sequencing and amplification using these polymerases. The following terms are commonly used by those skilled in the art of molecular biology.

Cloning vector. A nucleic acid molecule, for example a plasmid, cosmid or phage DNA or other DNA molecule, that is able to replicate autonomously in a host cell. A cloning vector may have one or a small number of recognition sites (e.g., recombination sites, restriction sites, topoisomerase sites, etc.) at which such DNA sequences may be manipulated in a determinable fashion without the loss of an essential biological function of the vector, and into which a nucleic acid segment of interest may be inserted in order to bring about its replication and cloning. The cloning vector may further contain a marker suitable for use in the identification of cells transformed with the cloning vector. Markers may be, for example, antibiotic resistance such as tetracycline resistance, ampicillin resistance or kanamycin resistance genes. Any other marker sequence known to those skilled in the art may be used.

Expression vector. A vector similar to a cloning vector but which is capable of enhancing the expression of a gene that has been cloned into it, after transfection into a host. The cloned gene is usually placed under the control of (i.e. operably linked to) certain control sequences such as promoter or enhancer sequences.

Host/recombinant host. Any prokaryotic cell, eukaryotic cell or microorganism that is the recipient of a replicable expression vector, cloning vector or any heterologous nucleic acid molecule which may or may not be integrated into host genomic DNA. The nucleic acid molecule may contain, a structural gene, or portion thereof, a promoter and/or an origin of replication. The terms "host" and "recombinant host" are also meant to include those host cells which have been genetically engineered to contain the heterologous nucleic acid sequences as part of the host chromosome or genome.

Promoter. A DNA sequence to which an RNA polymerase binds such that the polymerase, in the presence of the appropriate cofactors, initiates transcription at a transcriptional start site of a nucleic acid sequence to be transcribed. Promoters may include any 5' non-coding region that may be present between the transcriptional and translational start sites. Promoters may include cis-acting transcription control elements such as enhancers and other nucleotide sequences capable of interacting with transcription factors.

Operably linked. As used herein means that the promoter or other control sequence, such as an enhancer, is positioned to affect or control transcription of a nucleic acid sequence tow which it is associated in cis.

Expression. Expression is the process by which a polypeptide is produced from a nucleic acid. It may include transcription of a gene into mRNA and the translation of such mRNA into polypeptide(s).

Substantially pure. As used herein "substantially pure" refers to a protein that is essentially free from cellular contaminants which are associated with the desired protein in nature and may impair or enhance its function. Such contaminants include, but are not limited to, phosphatases, exonucleases, endonucleases or undesirable DNA polymerases. Substantially pure polypeptides can have 25% or less, 15% or less, 10% or less, 5% or less, or 1% or less contaminating cellular components. In some cases, substantially pure DNA polymerases have no detectable protein contaminants when 200 DNA polymerase units are run on a protein gel (e.g., SDS-PAGE) and stained with Coomassie blue.

Substantially isolated. As used herein "substantially isolated" refers to a polypeptide that is essentially free from contaminating proteins which may be associated with the polypeptide in nature and/or in a recombinant host. The substantially isolated peptide can have 25% or less, 15% or less, 10% or less, 5% or less, or 1% or less contaminating proteins. In some cases, substantially isolated polypeptides represent more than 75%, 85%, 90%, 95%, 98%, or 99% of the protein in a sample. The percentage of contaminating protein and/or protein of interest in a sample may be determined using techniques well known in the art (e.g., SDS-PAGE). In some cases, the substantially pure polypeptide has no detectable protein contaminants when 0.5 µg of a sample containing the polypeptide is analyzed by SDS-PAGE.

Substantially reduced. A recombinant enzyme "substantially reduced" in an enzymatic activity means that the enzyme has less than about 30%, less than about 20%, less than about 15%, less than about 10%, less than about 7.5%, less than about 5%, less than about 2% or less than about 1% of the activity of the corresponding (e.g., unmodified wild type) enzyme.

Primer. As used herein "primer" refers to a single stranded oligonucleotide that is extended by covalent bonding of nucleotide monomers during polymerization or amplification of a nucleic acid molecule.

Template. The term "template" as used herein refers to a double-stranded or single-stranded DNA or RNA substrate of a nucleic acid polymerase for amplification, synthesis, sequencing or copying. In the case of a double-stranded DNA molecule, denaturation of its strands to form a first and second strand is generally performed before amplification, synthesis or sequencing. A primer complementary to a portion of the template is hybridized to the template under appropriate conditions, and a polypeptide as described herein synthesizes a DNA molecule complementary to the template or portion thereof. Mismatch incorporation during the synthesis or extension of the newly synthesized DNA molecule may result in one or a number of mismatched base pairs. Thus, the synthesized DNA molecule need not be exactly complementary to the template. In the case of an RNA template, a DNA primer is hybridized to a strand of the template RNA and a polypeptide having reverse transcriptase activity is used to synthesize a complementary DNA.

Incorporating. The term "incorporating" refers to becoming part of a nucleic acid molecule or primer.

Amplification. As used herein "amplification" refers to any in vitro method for increasing the number of copies of a nucleotide sequence with the use of a DNA polymerase. Nucleic acid amplification results in the incorporation of nucleotides into a DNA molecule complementary to a template. The formed DNA molecule and its template can be used as templates to synthesize additional nucleic acid molecules. As used herein, one amplification reaction may consist of many rounds of DNA replication. DNA amplification reactions include, for example, PCR. One PCR reaction may consist of one or more e.g., 2, 3, 4, 5, 10, 15, 20, 25, 30, 50, 60, 70, 80, 90, 100 or more "cycles" of denaturation and synthesis of a DNA molecule.

Oligonucleotide. "Oligonucleotide" refers to a synthetic or natural molecule comprising a covalently linked series of nucleotides or nucleotide analogs. Such nucleotides or nucleotide analogs may be joined by a phosphodiester bond between the 3' position of the pentose and the 5' position of the pentose of the adjacent nucleotide. Also encompassed are molecules in which one or more internucleotide phosphate groups has been replaced by a different type of group, such as a peptide bond, a phosphorothioate group or a methylene group. Oligonucleotides may be synthetically prepared using protocols well known in the art.

Nucleotide. As used herein "nucleotide" refers to a base-sugar-phosphate combination. Nucleotides are monomeric units of a nucleic acid molecule (DNA and RNA). The term nucleotide includes deoxyribonucleoside triphosphates such as dATP, dCTP, DITP, dUTP, dGTP, dTTP, or derivatives thereof. Such derivatives include, for example, [α-S]dATP, 7-deaza-dGTP and 7-deaza-dATP. The term nucleotide as used herein also refers to dideoxyribonucleoside triphosphates (ddNTPs such as ddATP, ddCTP, ddGTP, ddITP and ddTTP) and their derivatives. A nucleotide may be unlabeled or detectable labeled by well known techniques. Detectable labels include, for example, radioactive isotopes, fluorescent labels, chemiluminescent labels, bioluminescent labels and enzyme labels. Nucleotides may also comprise one or more reactive functional groups. Labels may be attached to the functional group before, during and/or after use of the nucleotide in a nucleic acid synthesis, sequencing or amplification reaction.

A nucleotide may be unlabeled or detectably labeled by well known techniques. Detectable labels include, for example, radioactive isotopes, fluorescent labels, chemiluminescent labels and enzyme labels. Fluorescent labels of nucleotides include fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides include [R6G]dUTP, [TAMRA]dUTP, [R110] dCTP, [R6G]dCTP, [TAMRA]dCTP, [JOE]ddATP, [R6G] ddATP, [FAM]ddCTP, [R110]ddCTP, [TAMRA]ddGTP, and [dROX]ddTTP available from Perkin Elmer, Foster City, Calif.; FluoroLink DeoxyNucleotides, FluoroLink Cy3-dCTP, FluoroLink Cy5-dCTP, FluoroLink Fluor X-dCTP, Fluorolink Cy3-dUTP, and FluoroLink Cy5-dUTP available from Amersham, Arlington Heights, Ill.; Fluorescein-15-dATP, Fluorscein-12-dUTP, Tetramethyl-rhodamine-6- dUTP, IR$_{770}$-9-dATP, Fluorescein-12-ddUTP, Fluorescein-12-UTP, and Fluorescein-15-2'-dATP available from Boehringer Mannheim, Indianapolis, Ind.; and ChromaTide Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg.

Thermostable. As used herein "thermostable" refers to an activity of a molecule that is resistant to inactivation by heat. For example, DNA polymerases synthesize the formation of a DNA molecule complementary to a single-stranded DNA template by extending a primer in the 5'-to-3' direction. This activity for mesophilic DNA polymerases may be inactivated by heat treatment. For example, T5 DNA polymerase activity is totally inactivated by exposing the enzyme to a temperature of 90° C. for 30 seconds. A thermostable activity is more resistant to heat inactivation than a corresponding mesophilic activity. Thermostable polymerases are relatively stable to heat and are capable of catalyzing the formation of DNA or RNA from a nucleic acid template. A thermostable DNA polymerase need not be totally resistant to heat inactivation, but exhibits reduced activity as a consequence of heat treatment. A thermostable DNA polymerase typically will also have a higher optimum temperature than common mesophilic DNA polymerases.

A polymerase is considered especially thermostable when it retains at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95% of its polymerase activity after heating, for example, at 95° C. for 30 minutes.

Fidelity. Fidelity refers to the accuracy of nucleic acid polymerization, or the ability of a nucleic acid polymerase to discriminate correct from incorrect substrates when synthesizing nucleic acid molecules complementary to a template. The higher the fidelity of a polymerase, the less the polymerase misincorporates nucleotides in the growing strand during nucleic acid synthesis. An increase or enhancement in fidelity results in a more faithful polymerase having decreased error rate (i.e., decreased misincorporation rate).

Hybridization. The terms "hybridization" and "hybridizing" refer to pairing of two complementary single-stranded portions of nucleic acid molecules (RNA and/or DNA) to a double stranded form. As used herein, two nucleic acid molecule portions may be hybridized, although the base pairing is not completely complementary. Accordingly, mismatched bases do not prevent hybridization of two nucleic acid molecule portions provided that appropriate hybridization and stringency conditions, well known in the art, are used.

The ability of two nucleotide sequences to hybridize to each other is based upon a degree of complementarity of the two nucleotide sequences, which is in turn based on the fraction of matched complementary nucleotide pairs. The more nucleotides in a given sequence that are complementary to another sequence, the greater the degree of hybridization of one to the other. The degree of hybridization also depends on the conditions of stringency which include temperature, solvent ratios, salt concentrations, and the like.

"Selective hybridization" pertains to conditions where the degree of hybridization of a polynucleotide to a target would require complete or nearly complete complementarity; a degree of complementarity sufficient to ensure that the polynucleotide binds specifically to the target relative to binding other nucleic acids present in the hybridization medium.

5'-3' Exonuclease Activity. "5'-3' exonuclease activity" is an enzymatic activity often associated with DNA polymerases such as E. coli DNA polI and polIII. In many of the known polymerases, the 5'-3' exonuclease activity is present in the N-terminal region of the polymerase (Ollis et al, Nature 313:762-766, 1985; Freemont et al., Proteins 1:66-73, 1986; Joyce, Curr. Opin. Struct. Biol. 1:123-129, 1991). Amino acid determinants of 5'-3' exonuclease activity have been defined, e.g. for E. coli DNA polymerase I (Gutman et al., Nucl. Acids Res. 21:4406-4407, 1993). The 5'-exonuclease domain is dispensable for polymerase activity; e.g. as in the Klenow fragment of E. coli polymerase I. The Klenow fragment is a natural proteolytic fragment devoid of 5'-exonuclease activity (Joyce et al., J. Biol. Chem. 257:1958-1964, 1990). Polymerases lacking this activity are especially useful for DNA sequencing.

A DNA polymerase substantially reduced in 5'-3' exonuclease activity is either (1) a mutated DNA polymerase that has about or less than 10%, or about or less than 1%, of the 5'-3' exonuclease activity of the corresponding wild type enzyme, or (2) a DNA polymerase having a 5'-3' exonuclease specific activity which is less than about 1 unit/mg protein, or preferably about or less than 0.1 units/mg protein.

5'-3' exonuclease activity can be observed on sequencing gels. 5'-3' exonuclease activity can be measured by following the degradation of radiolabeled primers in a sequencing gel. Thus, the relative amounts of this activity, e.g. by comparing wild type and mutant polymerases, can be determined with no more than routine experimentation.

Oligonucleotide directed mutagenesis can be used to create mutant DNA polymerases. This technique allows for all possible base pair changes at any determined site along the encoding DNA molecule. In general, this technique involves annealing an oligonucleotide complementary (except for one or more desired mismatches) to a single stranded nucleotide sequence coding for the native DNA polymerase of interest. The mismatched oligonucleotide is then extended by DNA polymerase, generating a double stranded DNA molecule that contains the desired change in sequence on one strand. The changes in sequence can of course result in the deletion, substitution and/or insertion of an amino acid(s). The changed strand can be used as a template to form a double stranded polynucleotide. The double stranded polynucleotide can then be inserted into an appropriate expression vector, and a mutant polypeptide can thus be produced. The above-described oligonucleotide directed mutagenesis can be carried out using any technique known to those skilled in the art, for example, PCR. In one embodiment, mutations designed to alter the exonuclease activity do not adversely affect the polymerase activity.

DNA Polymerase Blends

DNA polymerase blends comprise at least two thermostable DNA polymerases, at least one of which is substantially reduced in 5'-exonuclease activity and at least one of which has 5'-exonuclease activity. By "exo+", it is meant that the DNA polymerase has 5'-exonuclease activity, and by "exo−" it is meant that the DNA polymerase is reduced or substantially reduced in 5'-exonuclease activity. The optimal 5'-exonuclease activity in a DNA polymerase blend may be obtained by combining different ratios of exo− and exo+ DNA polymerases. The optimal ratio will depend upon the particular polymerase blend being used and can be easily determined by one of ordinary skill in the art using the methods described herein.

The exo– mutants comprise at least one insertion, deletion, frame-shift mutation or point mutation. Deletion mutations can be N-terminal, C-terminal, and/or internal. In one embodiment, one or more point mutations, resulting in one or more amino acid substitutions, are used to produce polymerases substantially reduced in 5'-exonuclease activity. Such mutations may be made by a number of methods that will be familiar to one of ordinary skill, including but not limited to, site-directed mutagenesis. Site-directed mutagenesis allows for all possible classes of base pair changes at any determined site along the encoding DNA molecule. In general, this technique involves annealing an oligonucleotide complementary (except for one or more mismatches) to a single stranded nucleotide sequence encoding the DNA polymerase of interest. The mismatched oligonucleotide is then extended by DNA polymerase, generating a double stranded DNA molecule which contains the desired change in the sequence on one strand. The changes in sequence result in the deletion, substitution, or insertion of an amino acid. The double stranded polynucleotide is then inserted into an appropriate expression vector, and a mutant polypeptide is produced. This protocol may be carried out via PCR.

As mentioned above, The exo– and exo+ DNA polymerases may be the same polymerases (e.g., both Tfi polymerases), or may be different polymerases (e.g., Tfi and Tzi polymerases). In one embodiment, a Tfi polymerase having a point mutation resulting in substantially reduced 5'-exonuclease activity is used, In another embodiment, the Tfi exo– polymerase has an asp144 to ala144 (D144A) point mutation. In another embodiment, the polymerase has an asp121 to ala121 (D121A) point mutation. Although a D144A 5'-exonuclease mutant is exemplified herein, the use of any mutant DNA polymerase substantially reduced in 5'-exonuclease activity as a component of a DNA polymerase blend is within the scope of the present invention.

In addition to one or more mutations which substantially reduce the 5'-exonuclease activity of a DNA polymerase, the polymerase may also comprise one or more mutations resulting in increased thermostability. For example, in addition to a point mutation resulting in substantially reduced Tfi 5'-exonuclease activity, Tfi may also contain one or more mutations which result in increased thermostability. One of these mutations is glu437 to asp437 (E437D). In one embodiment, the Tfi DNA polymerase has two point mutations: D144A and E437D. This polymerase is both substantially reduced in exo– activity and has enhanced thermostability. Although a D144A/E437D double mutant is exemplified herein, the use of a mutant DNA polymerase substantially reduced in 5'-exonuclease activity and having enhanced thermostability (e.g., having any two point mutations which result in substantially reduced 5'-exo activity and enhanced thermostability) as a component of a DNA polymerase blend is within the scope of the present invention. The 5'-exonuclease activity and thermostability of any mutant polymerase may be determined using methods well known in the art and described herein. The exo–/exo+ DNA polymerase blends described herein may used at ratios of about 9:1, 8:2, 7:3, 6:4, 5:5, 4:6, 3:7, 2:8 or 1:9 (exo–:exo+). In one embodiment, the exo–/exo+ DNA polymerase blends are used at a ratio of about 7:3 (exo–:exo+).

Thermostable DNA polymerases contemplated for use in the compositions and methods described herein include, but are not limited to, *Thermus thermophilus* (Tth) DNA polymerase, *Thermus aquaticus* (Taq) DNA polymerase, *Thermococcus zilligi* (Tzi) DNA polymerase, *Thermotoga neopolitana* (Tne) DNA polymerase, *Thermotoga maritima* (Tma) DNA polymerase, *Thermus filiformis* (Tfi) DNA polymerase, Stoffel fragment, Thermoscript®, Superscript I®, Superscript II®, Superscript III®, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Pyrococcus* sp KOD2 (KOD) DNA polymerase, *Bacillus stearothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, a mycobacterium DNA polymerase (e.g. Mtb, Mlep); and generally Pol I and Pol III type polymerases, and mutants or variants thereof.

Such polymerases are described, for example, in U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; WO 97/09451; Barnes, W. M. Gene 112:29-35 (1992); Lawyer, F. C., et al, *PCR Meth. Appl.* 2:275-287, 1993; Flaman, J.-M, et al., *Nucl. Acids Res.* 22:3259-3260, 1994; and in U.S. patent application Ser. No. 10/244,081, filed Sep. 16, 2002. Tzi DNA polymerase is described in copending U.S. Patent Application Ser. No. 60/647,408, filed Jan. 28, 2005, the entire contents of which are incorporated herein by reference.

The complete nucleotide and amino acid sequence of wild type Tfi DNA polymerase (also known as *Thermus* Rt41A DNA polymerase) are provided herein as SEQ ID NO: 1 and 2, respectively, and also in Tables 15 and 16, respectively, of PCT WO 03/025132, and are incorporated herein by reference.

```
SEQ ID NO: 1:
5' atgcgaggtatgttaccactgtttgatctggaagaaccaccaaagcg cgtgttattagtggatggtcaccatttagcataccgcaccttctatgcat tatctttaacgacgagccgtggcgaaccggttcaaatggtttatggcttc gcacgctctttattaaaggcgttaaaggaggacggccaagcggttgtggt ggtcttcgatgcaaaggcacctagctttcgtcacgaagcatacgaggcgt ataaagcgggccgcgcaccaacccagaggactttccgcggcagctggcc ctggtgaaacgcttagtggacttattaggcctggttcgtttagaggcccc aggttatgaggcagatgatgtcctgggcaccttagcaaaaaaggccgagc gcgagggcatggaagtgcgtattttaaccggtgatcgtgatttttccaa ttattaagcgaaaaagtgtctgttttactgccggacggcaccttagttac cccgaaagatgtgcaggaaaaatacggtgttccgccggagcgttgggtcg attttcgtgcactgacgggtgatcgtagcgataacauccaggtgtcgcag gtattggtgagaaaaccgcgctgcgtttactggcggaatggggtagcgtg gaaaatttattaaagaatctggatcgtgttaagccggatagcgtccgccg caaaattgaagcccacttagaggatttacgtctgtctctggatttagcgc gtatccgtaccgacctgccgctggaggtcgacttcaaggcgctgcgccgc
```

-continued
```
cgcaccccggatttagaaggtttacgcgcctttctggaagagttagagtt cggttctctgctgcatgaatttggtctgttaggtggtgaaaagccacgcg aagaagccccgtggccgccaccggaaggcgcgtttgttggttttttactg tctcgtaaggaaccgatgtgggcggaattactggcattagcggcggcggc agagggtcgtgtgcatcgtgcaacctctccagtggaggcactggccgatt taaaggaagcacgcggttttctggcaaaagacctggccgttttagcgctg cgcgaaggcgttgcgctggatccgacggatgatccactgctggttgcata tttattagatccagcgaataccaatccagaaggtgttgcccgccgctatg gcggtgaatttacggaagatgcagcagagcgtgcgttactgagcgagcgt ctgtttcagaacttatttccgcgtctgtctgagaagttactgtggctgta tcaggaagtggaacgtccactgtctcgtgtcctggcgcacatggaggcac gtggcgttcgtctggacgtcccgctgttagaggcgctgtcttttgagctc gaaaaagagatggaacgcttagaaggtgaggtcttccgtctggcgggtca cccgtttaatctgaacagccgcgatcagttagagcgcgttctgttcgacg aattaggcctgacgccggtgggccgtaccgaaaagacgggtaagcgctct accgcccaaggtgcgctggaggcgctgcgcggtgcacacccaatcgtgga actgatcctgcaatatcgcgaactgtctaaactgaagtctacgtacttag acccattaccacgtttagttcacccgcgcaccggccgcctgcacacccgt tttaaccagacggcgaccgcaacgggccgcttaagctcttctgacccgaa cttacagaatattccagtgcgtaccccactgggtcagcgcattcgtaaag cattcgtggcggaagagggctggctgttattagccgcagattattctcag atcgaactgcgcgtgttagcccatttatctggcgacgagaatttaaaacg cgtctttcgtgaaggtaaggacatccataccgagacggcggcctggatgt tcggtctagatccggcactggttgacccaaaaatgcgccgtgcagcaaag acggtcaatttcggcgtgctgtacggtatgtctgcacaccgcttaagcca ggaactgggtattgattacaaagaggcggaggcattcattgagcgctatt tccagtctttcccgaaggtccgcgcctggatcgaacgtaccttagaggaa ggtcgtacccgtggctatgtggaaaccctgtttggccgccgtcgttatgt tccagatctggccagccgtgtgcgctctgtccgcgaggcagcagagcgta tggcatttaatatgccagtccaaggtacggccgcagatttaatgaagatc gctatggtgaagttattccacgcttaaaaccactgggcgcccacctgct gttacaagttcatgatgagcttgtgctggaggttccagaggatcgcgccg aggaagcaaaggccctggttaaggaagtgatggagaatacgtaccgctg gatgttccgctggaagttgaagttggtgtcggtcgagattggctcgaggc aaagggcgac-3'
```

SEQ ID NO: 2:
```
MRGMLPLFDLEEPPKRVLLVDGHHLAYRTFYALSLTTSRGEPVQMVYGFA

RSLLKALKEDGQAVVVVFDAKAPSFRHEAYEAYKAGRAPTPEDFPRQLAL

VKRLVDLLGLVRLEAPGYEADDVLGTLAKKAEREGMEVRILTGDRDFFQL

LSEKVSVLLPDGTLVTPKDVQEKYGVPPERWVDFRALTGDRSDNIPGVAG

IGEKTALRLLAEWGSVENLLKNLDRVKPDSVRRKIEAHLEDLRLSLDLAR

IRTDLPLEVDFKALRRRTPDLEGLRAFLEELEFGSLLHEFGLLGGEKPRE

EAPWPPPEGAFVGFLLSRKEPMWAELLALAAAAEGRVHRATSPVEALADL

KEARGFLAKDLAVLALREGVALDPTDDPLLVAYLLDPANTNPEGVARRYG

GEFTEDAAERALLSERLFQNLFPRLSEKLLWLYQEVERPLSRVLAHMEAR

GVRLDVPLLEALSFELEKEMERLEGEVFRLAGHPFNLNSRDQLERVLFDE

LGLTPVGRTEKTGKRSTAQGALEALRGAHPIVELILQYRELSKLKSTYLD

PLPRLVHPRTGRLHTRFNQTATATGRLSSSDPNLQNIPVRTPLGQRIRKA

FVAEEGWLLLAADYSQIELRVLAHLSGDENLKRVFREGKDIHTETAAWMF

GLDPALVDPKMRRAAKTVNFGVLYGMSAHRLSQELGIDYKEAEAFIERYF

QSFPKVRAWIERTLEEGRTRGYVETLFGRRRYVPDLASRVRSVREAAERM

AFNMPVQGTAADLMKIAMVKLFPRLKPLGAHLLLQVHDELVLEVPEDRAE

EAKALVKEVMENTYPLDVPLEVEVGVGRDWLEAKGD
```

Mutant Nucleic Acid Polymerases

Also described herein are isolated nucleic acids encoding polymerases having substantially reduced 5'-exonuclease activity, and which retain substantial levels of polymerase activity (e.g., point mutations of the isolated nucleic acid having the sequence of SEQ ID NO: 1 encoding wild type Tfi DNA polymerase). By "substantial levels" is meant at least about 25%, 30%, 35%, 40%, 45%, 50%, 55%, 60%, 65%, 70%, 75%, 80%, 85%, 90%, 95%, 96%, 97%, 98%, 99% or 100% of the polymerase activity of the corresponding wild type polymerase. In one embodiment, the nucleic acid encoding the mutant polymerase is operably linked to a promoter and/or inserted into a vector (e.g., an expression vector) as described below. In one embodiment, the nucleic acid encodes the DNA polymerase having the amino acid sequence of SEQ ID NO: 2 (wild type Tfi DNA polymerase).

Cloning and Expression of DNA Polymerases

To clone a gene encoding a DNA polymerase, isolated DNA (e.g. cDNA) comprising the polymerase gene of interest obtained from the appropriate cell type is used to construct a recombinant DNA library in a vector using conventional methods well known in the art of molecular biology (e.g., *Molecular Cloning, a Laboratory Manual* (2nd ed.), Cold Spring Harbor Laboratory Press, Cold Spring Harbor, N.Y., 1989. Any vector well known in the art can be used to clone a wild type or mutant DNA polymerase, as long as the vector is compatible with the host in which the recombinant DNA library is transformed.

To optimize expression of the polymerases described herein, inducible or constitutive promoters well known in the art may be used to express high levels of a polymerase structural gene in a recombinant host. Similarly, high copy number vectors, well known in the art, may be used to achieve high levels of expression. Vectors having an inducible high copy number may also be useful to enhance expression of the polymerases in a recombinant host.

Prokaryotic vectors for constructing the plasmid library include plasmids such as those capable of replication in *E. coli*, including, but not limited to, pBR322, pET-26b(+), ColE1, pSC101, pUC vectors (pUC18, pUC19, etc., in *Molecular Cloning, a Laboratory Manual*, Cold Spring Harbor Laboratory Press, Cold Spring Harbor, N.Y., 1989). *Bacillus* plasmids include pC194, pC221, pC217, etc. (Glyczan, in *Molecular Biology Bacilli*, Academic Press, New York, pp 307-329. 1982). Suitable *Streptomyces* plasmids include pIJ101 (Kendall et al., *J. Bacteriol.* 169:4177-4183, 1987). *Pseudomonas* plasmids are reviewed by John et al. (*Rad. Insec. Dis.* 8:693-704, 1986) and Igaki (*Jpn. J. Bacteriol.* 33:729-742, 1978). Broad-host range plasmids or cosmids, such as pCP13 (Darzins et al., *J. Bacteriol.* 159:9-18, 1984) can also be used for the present invention.

Wild type or mutant DNA polymerase genes may be cloned in a prokaryotic host such as *E. coli* or other bacterial species including, but not limited to, *Escherichia, Pseudomonas, Salmonella, Serratia*, and *Proteus*. Eukaryotic hosts also can be used for cloning and expression of wild type or mutant polymerases. Such hosts include yeast, fungi and mammalian cells. Expression of the desired DNA polymerase in such eukaryotic cells may involve the use of eukaryotic regulatory regions which include eukaryotic promoters. Cloning and expressing the wild type or mutant polymerase genes in eukaryotic cells may be accomplished by well known techniques using well known eukaryotic vector systems.

Hosts can be transformed by routine, well-known techniques. In one embodiment, transformed colonies are plated and screened for the expression of a thermostable DNA polymerase by transferring transformed *E. coli* colonies to nitrocellulose membranes. After the transformed cells are grown on nitrocellulose, the cells are lysed by standard techniques, and the membranes are then treated at 95° C. for 5 minutes to inactivate the endogenous *E. coli* enzyme. Other temperatures may be used to inactivate the host polymerases depending on the host used and the temperature stability of the DNA polymerase to be cloned. Stable DNA polymerase activity is then detected by assaying for the presence of DNA polymerase activity using well known techniques (i.e. Sanger et al., *Gene* 97:119-123, 1991).

Also described herein are host cells that contain or comprise such nucleic acid molecules, and vectors that contain or comprise these nucleic acid molecules. Also included are methods for making the polypeptides (e.g., methods for producing polypeptides using these nucleic acid molecules). In particular embodiments, polypeptides are provided in (1) isolated, (2) substantially pure, and/or (3) essentially pure forms. Other aspects include compositions and mixtures (e.g., reaction mixtures) that contain or comprise one or more polypeptides and/or more polynucleotides described herein.

To optimize expression of the wild type or mutant DNA polymerases, inducible or constitutive promoters are well known and may be used to express high levels of a polymerase structural gene in a recombinant host. Similarly, high copy number vectors, well known in the art, may be used to achieve or enhance expression of the DNA polymerase in a recombinant host.

To express the desired structural gene in a prokaryotic cell (such as, *E. coli, B. subtilis, Pseudomonas*, etc.), the gene may be operably linked to a functional prokaryotic promoter. However, the natural promoter may function in prokaryotic hosts allowing expression of the polymerase gene. Thus, the natural promoter or other promoters may be used to express the DNA polymerase gene. Such other promoters may be used to enhance expression and may either be constitutive or regulatable (i.e., inducible or derepressible) promoters. Examples of constitutive promoters include the int promoter of bacteriophage λ, and the bla promoter of the β-lactamase gene of pBR322. Examples of inducible prokaryotic promoters include the major right and left promoters of bacteriophage λ ($P_R$ and $P_L$), trp, recA, lacZ, lacI, tet, gal, trc, and tac promoters of *E. coli*. The *B. subtilis* promoters include α-amylase (Ulmanen et al., *J. Bacteriol* 162:176-182 (1985)) and *Bacillus* bacteriophage promoters (Gryczan, T., supra.). *Streptomyces* promoters are described by Ward et al., *Mol. Gen. Genet.* 203:468-478, 1986). Prokaryotic promoters are also reviewed by Glick, *J. Ind. Microbiol.* 1:277-282, 1987; Cenatiempto, Y., *Biochimie* 68:505-516, 1986; and Gottesman, *Ann. Rev. Genet.* 18:415-442 (1984). Expression in a prokaryotic cell also requires the presence of a ribosomal binding site upstream of the gene-encoding sequence. Such ribosomal binding sites are disclosed, for example, by Gold et al., *Ann. Rev. Microbiol.* 35:365-404 (1981).

In one embodiment, the DNA polymerases described herein are produced by fermentation of the recombinant host containing and expressing the cloned polymerase gene. Any nutrient that can be assimilated by the thermophile of interest, or a host containing the cloned DNA polymerase gene, may be added to the culture medium. Optimal culture conditions should be selected case by case according to the strain used and the composition of the culture medium. Antibiotics may also be added to the growth media to insure maintenance of vector DNA containing the desired gene to be expressed.

Recombinant host cells producing the DNA polymerase of this invention can be separated from liquid culture, for example, by centrifugation. In general, the collected microbial cells are dispersed in a suitable buffer, and then broken down by ultrasonic treatment or by other well known procedures to allow extraction of the enzymes by the buffer solution. After removal of cell debris by ultracentrifugation or centrifugation, the DNA polymerase can be purified by standard protein purification techniques such as extraction, precipitation, chromatography, affinity chromatography, electrophoresis or the like. Assays to detect the presence of the DNA polymerase during purification are well known in the art and can be used during conventional biochemical purification methods to determine the presence of these enzymes.

Use of exo−/exo+ Polymerase Blends and Mutant Polymerases

The exo−/exo+ DNA polymerase blends, or mutant polymerases described herein may be used in well known DNA sequencing, DNA labeling, DNA amplification or cDNA synthesis reactions. The polymerase blends and polymerases may also be used to analyze and/or type polymorphic DNA fragments. The DNA may be obtained from any desired source as described below.

Sources of DNA

Suitable sources of DNA, including a variety of cells, tissues, organs or organisms, may be obtained through any number of commercial sources (including American Type Culture Collection (ATCC), Rockville, Md.; Jackson Laboratories, Bar Harbor, Me.; Cell Systems, Inc., Kirkland, Wash.; Advanced Tissue Sciences, La Jolla, Calif.). In one embodiment, cells that used as starting materials for genomic DNA preparation are eukaryotic (including fungi or yeasts, plants, protozoans and other parasites, and animals including humans and other mammals). Any mammalian cell may be used for preparation of DNA, including blood cells (erythrocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells), although other cells, including the progenitors, precursors and stem cells that give rise to the above-described somatic cells, are equally suitable. Also suitable for use in the preparation of DNA are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus. These cells, tissues and organs may be normal, or they may be pathological.

DNA Sequencing

As is well known, sequencing reactions (isothermal DNA sequencing and cycle sequencing of DNA) require the use of DNA polymerases. Dideoxy-mediated sequencing involves the use of a chain-termination technique which uses a specific polymer for extension by DNA polymerase, a base-specific chain terminator and the use of polyacrylamide gels to separate the newly synthesized chain-terminated DNA molecules by size so that at least a part of the nucleotide sequence of the original DNA molecule can be determined. Specifically, a DNA molecule is sequenced by using four separate DNA sequence reactions, each of which contains different base-specific terminators. For example, the first reaction will contain a G-specific terminator, the second reaction will contain a T-specific terminator, the third reaction will contain an A-specific terminator, and a fourth reaction may contain a C-specific terminator. Preferred terminator nucleotides include dideoxyribonucleoside triphosphates (ddNTPs) such as ddATP, ddTTP, ddGTP, ddITP and ddCTP. Analogs of dideoxyribonucleoside triphosphates may also be used and are well known in the art.

When sequencing a DNA molecule, ddNTPs lack a hydroxyl residue at the 3' position of the deoxyribose base and thus, although they can be incorporated by DNA polymerases into the growing DNA chain, the absence of the 3'-hydroxy residue prevents formation of the next phosphodiester bond resulting in termination of extension of the DNA molecule. Thus, when a small amount of one ddNTP is included in a sequencing reaction mixture, there is competition between extension of the chain and base-specific termination resulting in a population of synthesized DNA molecules which are shorter in length than the DNA template to be sequenced. By using four different ddNTPs in four separate enzymatic reactions, populations of the synthesized DNA molecules can be separated by size so that at least a part of the nucleotide sequence of the original DNA molecule can be determined. DNA sequencing by dideoxy-nucleotides is well known and is described by Sambrook et al., supra. As will be readily recognized, the exo–/exo+ DNA polymerase blends and mutant DNA polymerases described herein may be used in such sequencing reactions.

As is well known, detectably labeled nucleotides are typically included in sequencing reactions. Any number of labeled nucleotides can be used in sequencing (or labeling) reactions, including, but not limited to, radioactive isotopes, fluorescent labels, chemiluminescent labels, bioluminescent labels, and enzyme labels.

Polymerase Chain Reaction (PCR)

Polymerase chain reaction (PCR), a well known DNA amplification technique, is a process by which DNA polymerase and deoxyribonucleoside triphosphates are used to amplify a target DNA template. In such PCR reactions, two primers, one complementary to the 3' termini (or near the 3'-termini) of the first strand of the DNA molecule to be amplified, and a second primer complementary to the 3' termini (or near the 3'-termini) of the second strand of the DNA molecule to be amplified, are hybridized to their respective DNA strands. After hybridization, DNA polymerase, in the presence of deoxyribonucleoside triphosphates, allows the synthesis of a third DNA molecule complementary to the first strand and a fourth DNA molecule complementary to the second strand of the DNA molecule to be amplified. This synthesis results in two double stranded DNA molecules. Such double stranded DNA molecules may then be used as DNA templates for synthesis of additional DNA molecules by providing a DNA polymerase, primers, and deoxyribonucleoside triphosphates. As is well known, the additional synthesis is carried out by "cycling" the original reaction (with excess primers and deoxyribonucleoside triphosphates) allowing multiple denaturing and synthesis steps. Typically, denaturing of double stranded DNA molecules to form single stranded DNA templates is accomplished by high temperatures. The exo–/exo+ DNA polymerase blends and mutant DNA polymerases described herein are heat stable, and thus will survive such thermal cycling during DNA amplification reactions. Thus, these DNA polymerase blends and mutated DNA polymerases are ideally suited for PCR reactions, particularly where high temperatures are used to denature the DNA molecules during amplification. The exo–/exo+ polymerase blends and mutated DNA polymerases described herein may be used in all PCR methods known to one of ordinary skill in the art, including end-point PCR, real-time qPCR (U.S. Pat. Nos. 6,569,627; 5,994,056; 5,210,015; 5,487,972; 5,804,375; 5,994,076, the contents of which are incorporated by reference in their entirety), allele specific amplification, linear PCR, one step reverse transcriptase (RT)-PCR, two step RT-PCR, mutagenic PCR, multiplex PCR and the PCR methods described in copending U.S. patent application Ser. No. 09/599,594, the contents of which are incorporated by reference in their entirety.

Preparation of cDNA

The exo–/exo+ DNA polymerase blends and mutant DNA polymerases described herein may also be used to prepare cDNA from mRNA templates. See, for example, U.S. Pat. Nos. 5,405,776 and 5,244,797, the disclosures of which are incorporated herein by reference. Thus, the invention also relates to a method of preparing cDNA from mRNA, comprising (a) contacting mRNA with an oligo(dT) primer or other complementary primer to form a hybrid; and (b) contacting the hybrid formed in step (a) with the DNA polymerase blends or mutant polymerases of the invention and the four dNTPs, whereby a cDNA-RNA hybrid is obtained. If the reaction mixture is step (b) further comprises an appropriate oligonucleotide which is complementary to the cDNA being produced, it is also possible to obtain dsDNA following first strand synthesis. Thus, the invention is also directed to a method of preparing dsDNA with the exo–/exo+ DNA polymerase blends and polymerases described herein.

Another embodiment features compositions and reactions for nucleic acid synthesis, sequencing or amplification that include exo–/exo+ DNA polymerase blends and mutant DNA polymerases. These mixtures include the polymerase blend or mutant polymerase, one or more dNTPs (dATP, dTTP, dGTP, dCTP), a nucleic acid template, an oligonucleotide primer, magnesium and buffer salts, and may also include other components (e.g., nonionic detergent). If sequencing reactions are performed, the reaction may also include one or more ddNTPs. The dNTPs or ddNTPs may be unlabeled or labeled with a fluorescent, chemiluminescent, bioluminescent, enzymatic or radioactive label. In some embodiments, compositions comprising DNA polymerase blends or mutant DNA polymerases are formulated as described in PCT WO98/06736, the entire contents of which are incorporated herein by reference.

In some embodiments, kits are provided (e.g., for use in carrying out the methods described herein). Such kits may include, in addition to the exo–/exo+ DNA polymerase blends or mutant DNA polymerase, one or more one or more components selected from the group consisting of: one or more anti-DNA polymerase antibodies, one or more host cells (preferably competent to take up nucleic acid molecules), one or more nucleic acids (e.g., nucleic acid templates), one or more nucleotides, one or more nucleic acid primers, one or more vectors, one or more ligases, one or more topoisomerases, and one or more buffers or buffer salts.

Analyzing and Typing Polymorphic DNA Fragments

In one embodiment, the relationship between a first individual and a second individual may be determined by analyzing and typing a particular polymorphic DNA fragment, such as a minisatellite or microsatellite DNA sequence. In such a method, the amplified fragments for each individual are compared to determine similarities or dissimilarities. Such an analysis is accomplished, for example, by comparing the size of the amplified fragments from each individual, or by comparing the sequence of the amplified fragments from each individual. In another aspect of the invention, genetic identity can be determined. Such identity testing is important, for example, in paternity testing, forensic analysis, etc. In this aspect of the invention, a sample containing DNA is analyzed and compared to a sample from one or more individuals. In one such aspect of the invention, one sample of DNA may be derived from a first individual and another sample may be derived from a second individual whose relationship to the first individual is unknown; comparison of these samples from the first and second individuals by the methods of the invention may then facilitate a determination of the genetic identity or relationship between the first and second a individual. In a particularly preferred such aspect, the first DNA sample may be a known sample derived from a known individual and the second DNA sample may be an unknown sample derived, for example, from crime scene material. In an additional aspect of the invention, one sample of DNA may be derived from a first individual and another sample may be derived from a second individual who is related to the first individual; comparison of these samples from the first and second individuals by the methods of the invention may then facilitate a determination of the genetic kinship of the first and second individuals by allowing examination of the Mendelian inheritance, for example, of a polymorphic, minisatellite, microsatellite or STR DNA fragment.

In another aspect of the invention, DNA fragments important as genetic markers for encoding a gene of interest can be identified and isolated. For example, by comparing samples from different sources, DNA fragments which may be important in causing diseases such as infectious diseases (of bacterial, fungal, parasitic or viral etiology), cancers or genetic diseases, can be identified and characterized. In this aspect of the invention a DNA sample from normal cells or tissue is compared to a DNA sample from diseased cells or tissue. Upon comparison according to the invention, one or more unique polymorphic fragments present in one DNA sample and not present in the other DNA sample can be identified and isolated. Identification of such unique polymorphic fragments allows for identification of sequences associated with, or involved in, causing the diseased state.

Gel electrophoresis is typically performed on agarose or polyacrylamide sequencing gels according to standard protocols using gels containing polyacrylamide at concentrations of 3-12% (e.g., 8%), and containing urea at a concentration of about 4-12M (e.g., 8M). Samples are loaded onto the gels, usually with samples containing amplified DNA fragments prepared from different sources of genomic DNA being loaded into adjacent lanes of the gel to facilitate subsequent comparison. Reference markers of known sizes may be used to facilitate the comparison of samples. Following electrophoretic separation, DNA fragments may be visualized and identified by a variety of techniques that are routine to those of ordinary skill in the art, such as autoradiography. One can then examine the autoradiographic films either for differences in polymorphic fragment patterns ("typing") or for the presence of one or more unique bands in one lane of the gel ("identifying"); the presence of a band in one lane (corresponding to a single sample, cell or tissue type) that is not observed in other lanes indicates that the DNA fragment comprising that unique band is source-specific and thus a potential polymorphic DNA fragment.

Kits

The exo−/exo+ DNA polymerase blends and mutant polymerases described herein are suited for the preparation of a kit. Kits comprising these polymerase blends or polymerases may be used for detectably labeling DNA molecules, DNA sequencing, amplifying DNA molecules or cDNA synthesis by well known techniques, depending on the content of the kit. See U.S. Pat. Nos. 4,962,020, 5,173,411, 4,795,699, 5,498,523, 5,405,776 and 5,244,797, the disclosures of which are hereby incorporated by reference. Such kits may comprise a carrying means being compartmentalized to receive in close confinement one or more container means such as vials, test tubes and the like. Each of such container means comprises components or a mixture of components needed to perform DNA sequencing, DNA labeling, DNA amplification, or cDNA synthesis.

Such kits may include, in addition to an exo−/exo+ DNA polymerase blend or mutant DNA polymerase, one or more one or more components selected from the group consisting of: one or more anti-DNA polymerase antibodies, one or more host cells (preferably competent to take up nucleic acid molecules), one or more nucleic acids (e.g., nucleic acid templates), one or more nucleotides, one or more nucleic acid primers, one or more vectors, one or more ligases, one or more topoisomerases, and one or more buffers or buffer salts.

Kit constituents typically are provided, individually or collectively, in containers (e.g., vials, tubes, ampules, and bottles). Kits typically include packaging material, including instructions describing how the kit can be used for example to synthesize, amplify or sequence nucleic acids. A first container may, for example, comprise a substantially purified sample of each polymerase. A second container may comprise one or a number of types of nucleotides needed to synthesize a DNA molecule complementary to DNA template. A third container may comprise one or a number of different types of dideoxynucleoside triphosphates. A fourth container may comprise pyrophosphatase. In addition to the above containers, additional containers may be included in the kit which comprise one or a number of DNA primers. A kit used for amplifying DNA will comprise, for example, a first container comprising a substantially pure exo− and exo+ DNA polymerase, or a substantially pure exo− DNA polymerase, as described herein and one or a number of additional containers which comprise a single type of nucleotide or mixtures of nucleotides. Various primers may or may not be included in a kit for amplifying DNA. The various kit components need not be provided in separate containers, but may also be provided in various combinations in the same container. For example, the exo−/exo+ polymerases and nucleotides may be provided in the same container, or the exo−, exo+ and nucleotides may be provided in different containers.

Kits for cDNA synthesis comprise a first container containing an exo−/exo+ polymerase blend, a second container containing the four dNTPs and the third container containing an oligo(dT) primer. See U.S. Pat. Nos. 5,405,776 and 5,244,797, the disclosures of which are incorporated herein by reference. Since the exo−/exo+ DNA polymerase blends and exo− DNA polymerases of the present invention are also capable of preparing dsDNA, a fourth container may contain an appropriate primer complementary to the first strand cDNA. Of course, it is also possible to combine one or more of these reagents in a single tube. When desired, the kit of the present invention may also include a container which comprises detectably labeled nucleotides which may be used during the synthesis or sequencing of a DNA molecule. One of a number of labels may be used to detect such nucleotides. Illustrative labels include, but are not limited to, radioactive isotopes, fluorescent labels, chemiluminescent labels, bioluminescent labels and enzyme labels.

Having now generally described the embodiments, the same will be more readily understood through reference to the following examples which are provided by way of illustration, and are not intending to be limiting of the present invention.

EXAMPLES

Example 1

Synthesis of Tfi Gene

The Tfi gene was synthesized from 136 nucleotides by PCR-based gene assembly (Young et al, *Nucl. Acids Res.*, 2004). The oligonucleotides were designed using the program DNA Works 2.0 (Hoover et al., 2002). The protein sequence of Tfi was input into DNA Works and the parameters were adjusted to optimize expression in *E. coli* and to minimize the GC content of the synthetic gene. The fully synthesized gene product, containing the mutation E437D (GAA→GAT), was verified by sequencing and subcloned into the pTTQ vector at the NdeI/Hind/III restriction sites. This is referred to as Tfi 5'-exo+(or exo+). Tfi 5'-exo− (or exo−) contains an additional mutation in the 5'→3' exonuclease domain, D144A (GAT→GAA), and was introduced into Tfi exo+ using the Quikchange site-directed mutagenesis kit (Stratagene) according to the manufacturer's instructions. The DNA sequence of the Tfi open reading frame is shown in SEQ ID NO: 1, and the wild type Tfi protein sequence is shown in SEQ ID NO: 2.

Example 2

Tfi Cell Culture

For a 6 liter preparation, 6 1 L Tfi cultures were grown in 3 1 shaker flasks containing LB-Ampicillin (LB-amp) (100 µg/ml). The cultures were incubated at 37° C. with constant shaking at 250 rpm. The two strains used were:
Tfi exo+ strain: pTTQ-Tfi-E437D in DH10b
Tfi exo− strain: pTTQ-Tfi-E437D/D144A in DH10b On day 1, a starter culture was made in which 200 ml LB-amp (100 µg/ml) was inoculated with a glycerol stock of DH10b (pTTQ-sRT41a-E437D/D144A). Cells were grown overnight at 37° C., 250 rpm. On day 2, the diluted starter culture was diluted 1:30 into six 1 L LB-amp (100 µg/ml) shaker flasks at 37° C., 250 rpm for 6-8 hours until the $OD_{600}$ was about 1.0. Protein expression was induced with 1 mM IPTG, and continued overnight for 14-16 hours at 37° C., 250 rpm. Cells were centrifuged and the supernatant was discarded. The cell pellet was either frozen at −80° C. or processed as described in Example 2. Active polymerase was prepared from both frozen and fresh cell paste with no discernable difference in specific activity. The weight of the cells was about 4 g cell paste/L culture.

Example 3

Purification of Tfi DNA Polymerases (Exo+ and Exo−)

Cells were suspended in lysis buffer (50 mM Tris-HCl, pH 7.5, 10 mM KCl, 1 mM EDTA, 6% glycerol, 1 ml/20 g cell paste protease inhibitor cocktail and 5 mM 2-mercaptoethanol) and passaged through a French press, resulting in about 85% cell lysis. The samples were centrifuged, and Big Chaps and CHAPSO were added to the lysate to concentrations of 0.001% and 0.0001%, respectively. Lysates were then heated for 20 min at 75° C., with mixing at 10 min. The resulting lysate was precipitated with polyethyleneimine (Polymin P) by adding 5M NaCl to a Cf=0.2M, then adding 10% Polymin P at 4° C., while stirring, to a Cf=0.4%. Samples were stirred for 15-20 min, then centrifuged at 15,000 rpm for 15 min. The resulting lysates were precipitated with ammonium sulfate by adding solid ammonium sulfate to 45% (258 g/1 L), then stirred at 4° C. for 30 min. The samples were centrifuged at 15,000 rpm for 20 min at 4° C. The ammonium sulfate pellet was resuspended in 12 ml buffer B (25 mM Kpi, pH 6.6, 50 mM KCl, 0.1 mM EDTA, 8% glycerol, 5 mM 2-mercaptoethanol, 0.001% Big CHAPS, 0.0001% CHAPSO), then dialyzed overnight in 1 L buffer B.

The resulting samples were then subjected to $EMD-SO_4$ column chromatography using 5.0 mL bed volume columns (EM Science, catalog #116882-7) equilibrated in buffer B. Pump A pumped buffer B, and pump B pumped buffer C (25 mM Kpi, pH 6.6, 700 mM KCl, 0.1 mM EDTA, 8% glycerol, 5 mM 2-mercaptoethanol, 0.001% Big CHAPS, 0.0001% CHAPSO). 12 ml sample was filtered through a 0.45 µm syringe filter and applied to the column at a flow rate of 1 ml/min and a gradient of 0-70% buffer B over 15 column volumes. Fraction sizes were 2 ml. The presence of Tfi DNA polymerase in the fractions was monitored by sodium dodecyl sulfate-polyacrylamide gel electrophoresis (SDS-PAGE) on a 4-20% tris-glycine gel and visualization of a 94 kDa band which is the approximate molecular weight of Tfi DNA polymerase. Peak fractions containing the polymerase were pooled and dialyzed overnight in 1 L of buffer D (25 mM Tris-Cl, pH 8.0, 50 mM KCl, 0.1 mM EDTA, 8% glycerol, 5 mM 2-mercaptoethanol, 0.001% Big CHAPS, 0.0001% CHAPSO).

The resulting samples were then subjected to Source 30Q column chromatography (Amersham) on a 5 ml bed volume column with a 2.0 cm diameter. Column was equilibrated in buffer D. Pump A pumped buffer D, and pump B pumped buffer E (25 mM Tris HCl, pH 8.0; 500 mM KCl, 0.1 mM EDTA, 8% glycerol, 5 mM 2-mercaptoethanol, 0.001% Big CHAPS, 0.0001% CHAPSO). 20 ml sample was filtered through a 0.45 µm syringe filter and applied to the column at a flow rate of 1 ml/min and a gradient of 0-100% buffer B over 15 column volumes. Fraction sizes were 2 ml. Peak fractions were pooled and dialyzed overnight in Tfi storage buffer (20 mM Tris-HCl, pH 8.0, 0.1 mM EDTA; 50% glycerol, 1 mM DTT, 0.1% Big CHAPS, 0.01% CHAPSO).

Example 4

PCR Optimization

Taq 10× PCR buffer was used as a starting point for PCR optimization. The final 5× Tfi buffer was 250 mM Tris-HCl, pH 8.4, 75 mM $(NH_4)_2SO_4$, 25 mM KCl, 10% glycerol, 0.5% Big CHAPS, 0.05% CHAPSO, 1 mM DTT. Tfi PCR reactions consisted of 0.2 µM primers, 200 µM each dNTP, 1× Tfi PCR buffer, 1.5 mM $MgCl_2$, 20-200 ng template DNA, 1-5 units Tfi DNA polymerase (total volume=50 µl). Cycling conditions were 35 cycles at 94° C. for 15-30 s, 55° C.-64° C. for 30 s, and 72° C. for 1 min/kb. 10 µl of the PCR reactions were analyzed on agarose gels containing 0.4 ug/ml ethidium bromide (EtBr).

Example 5

Fidelity Determination

Polymerase fidelity was determined using BRCA1 exon 11 PCR amplification and dHPLC analysis. Amplification reactions were set up using different DNA polymerases. Briefly, a 437 base pair fragment was amplified in a reaction consisting of 100 ng K562 genomic DNA, 0.2 µM of each primer, 1×PCR reaction buffer, 1.5 mM $Mg^{2+}$, 200 µM of each DNTP and water in a final volume of 50 µl. The forward primer was 5'-GAAACTGCCATGCTCAGAGA-3' (SEQ ID NO: 3) and the reverse primer was 5'-A-TTATTTGTGAGGGGACGC-3' (SEQ ID NO: 4). Cycling conditions were 94° C. for 2 min, 35 cycles of 94° C., 15 s; 58° C., 30 s; 68° C., 45 s; followed by 68° C. for 7 min and then 4° C. Five µl of the reaction mix was directly loaded onto the WAVE system after PCR cycling. A solvent gradient was generated by mixing WAVE Optimized™ buffer A (0.1 M ETAA, pH 7.0) and WAVE Optimized™ buffer B (0.1 M ETAA, 25% acetonitrile, pH 7.0) in a linear gradient running from 60 to 66% Buffer B over 4.5 minutes at 56° C. Following each analytical run, a DNASep™ Cartridge was washed using 100% WAVE optimized buffer B for 0.5 min, then equilibrated at 54% Buffer B for two minutes in preparation for the next sample injection. Peak areas for homo- and heteroduplex peaks were calculated to allow determination of the percentage of PCR fragments forming heteroduplex DNA, an indication of the presence of PCR-induced errors.

A representative chromatogram is shown in FIG. 1. The percentage of each peak is shown in the graph. The major, homoduplex peak was about 72%, 65% and 65% for Tfi exo-/exo+ (7:3 ratio). Taq (Invitrogen) and Taq (Promega), respectively.

Example 6

PCR using Tfi Exo-/Exo+ Blends

Figure 2:
FIG. 2 is a photograph of an agarose gel showing PCR amplification products of the Rhod 1495 gene using different ratios of 5'-(exo+) and 5'-(exo-) Tfi DNA polymerases. For each reaction, 5 units of enzymes having different exo-:exo+ ratios were added. The ratios shown at the top of the gel are exo-:exo+. Ten µl of each reaction was analyzed on agarose gels containing ethidium bromide.

PCR was performed on human K562 cell genomic template DNA to amplify a 1.5 kb target (Rhod 1495). Each reaction was set up with a reaction buffer of 50 mM Tris HCl, pH 8.4, 15 mM $(NH_4)_2SO_4$, 5 mM KCl, 2% glycerol, 0.2 mM of each DNTP, 1.5 mM $MgCl_2$, 0.02% Big Chap, 0.002% Chapso, 0.2 mM DTT, 0.2 µM of each primer and 100 ng K562 genomic DNA. The Rhodl495 forward primer was 5'-CAGCCCCTTCGAGTACCCACAGT-3' (SEQ ID NO: 5), and the reverse primer was 5'-TGCTCACCACCCCAT-GAAGTTT-3' (SEQ ID NO: 6). Two enzymes were used for the PCR reactions: Tfi exo- (D144A/E437D) and Tfi exo+ (E437D) DNA polymerases. The complete nucleotide and amino acid sequence of Tfi DNA polymerase may be found in copending U.S. patent application Ser. No. 10/244,081, the entire contents of which are incorporated herein by reference. For each reaction, 5 units of polymerase with different ratios of exo- to exo+ were added to the reaction mixture: exo-only, 9:1, 8:2, 7:3, 6:4, 5:5, 4:6, 3:7, 2:8, 1:9 and exo+ (represented as ratios of exo- to exo+). Cycling conditions (Perkin Elmer 9600 thermal cycler) were 1 cycle of 94° C. for 30 sec, followed by 35 cycles of 94° C., 30s; 35 cycles of 94° C. for 15 s, 60° C. for 30 s; and 68° C. for 1.5 min; then 1 cycle of 68° C. for 10 min. Ten µl of the PCR reaction products were analyzed on agarose gels containing 0.4 µg/ml ethidium bromide. The results are shown in FIG. 2. Thus, the addition of the exo- Tfi polymerase increased the PCR product yield.

Example 7

Real-Time PCR

Real-time PCR was used to amplify a TaqMan® human β-actin target. Each Tfi DNA polymerase reaction was set up with a reaction buffer containing 50 mM Tris-HCl, pH 8.4, 15 mM $(NH_4)_2SO_4$, 2% glycerol, 5 mM KCl, 0.02% Big Chap, 0.002% Chapso, 0.2 mM DTT, 3 mM $MgCl_2$, 0.5 mM of each DNTP, 0.2 µM each β-actin primer (see below), 1×ROX reference dye, 3.5 units of Tfi exo-, 1.5 units of Tfi exo+ and a different copy number of plasmid DNA as a template.

Each Taq DNA polymerase reaction was set up with a reaction buffer containing 20 mM Tris-HCl, pH 8.4, 50 mM KCl, 3 mM $MgCl_2$, 0.5 mM of each dNTP, 0.2 µM each β-actin primer (see below), 0.1 µM β-actin probe (see below), 1×ROX reference dye, 1 unit of Taq DNA polymerase and a different copy number of plasmid DNA as a template. The β-actin primer and probe sequences used were:

```
                                          (SEQ ID NO: 7)
Forward:  5'-CCTGGCACCCAGCACAAT-3'

(SEQ ID NO: 8)
Reverse:  5'-GGGCCGGACTCGTCATAC-3'

(SEQ ID NO: 9)
Probe:    5'-(FAM) AGCCGCCGATCCACACGAGT (TAMRA)-3'
```

The cycling conditions were 50° C. for 2 min, 95° C. for 2 min, followed by 50 cycles of 95° C. for 15 s, 60° C. for 30 s. The results are shown in Table 1 (Taq DNA polymerase) and Table 2 (Tfi exo-/exo+ DNA polymerase). The numbers shown in the top row of each table are the copy numbers of plasmid DNA used as a PCR template. NTC non-treated control.

TABLE 1

|          | $10^6$ | $10^5$ | $10^4$ | $10^3$ | $10^2$ | $10^1$ | NTC |
|----------|--------|--------|--------|--------|--------|--------|-----|
| sample 1 | 20.53  | 24.37  | 28.32  | 30.77  | 34.44  | 38.14  | undet. |
| sample 2 | 20.79  | 24.34  | 27.41  | 31.00  | 33.77  | 39.96  | undet. |
| sample 3 | 20.71  | 24.01  | 28.32  | 31.34  | 34.49  | 37.46  | undet. |
| average  | 20.68  | 24.24  | 28.02  | 31.03  | 34.23  | 38.52  | No amp. |
| st. dev. | 0.13   | 0.20   | 0.52   | 0.29   | 0.40   | 1.30   | |

TABLE 2

|          | $10^6$ | $10^5$ | $10^4$ | $10^3$ | $10^2$ | $10^1$ | NTC |
|----------|--------|--------|--------|--------|--------|--------|-----|
| sample 1 | 21.54  | 25.47  | 29.00  | 31.97  | 35.08  | 38.90  | undet. |
| sample 2 | 21.67  | 24.66  | 28.93  | 31.18  | 33.92  | 38.02  | undet. |
| sample 3 | 20.87  | 23.90  | 28.42  | 31.69  | 34.13  | 40.66  | undet. |
| average  | 21.36  | 24.67  | 28.78  | 31.61  | 34.38  | 39.19  | No amp. |
| st. dev. | 0.43   | 0.78   | 0.31   | 0.40   | 0.62   | 1.34   | |

For $10^6$-100 copies, the slopes were -3.39 and -3.30 for Tfi and Taq, respectively. The correlation coefficients (R2) for Tfi and Taq, respectively, were 0.995 and 0.986 These results show that Tfi exo-/exo+ DNA polymerase blend works as well as Taq DNA polymerase in real-time PCR.

Example 8

Use of Non-Ionic Detergents in Tfi Exo−/Exo+ PCR Reactions

Over 100 different nonionic detergents were screened for their compatibility with Tfi exo−/exo+ PCR reactions. Suitable detergents included NP-40, Triton X-100, Chaps, Chapso, N-dodecyl-N,N-dimethylamine-N-oxide, Big CHAPS(N,N-bis-(3-D-gluconamidopropyl)cholamide), N-tetradecyl-N,N-dimethylamine-N-oxide, N-decyl-β-D-maltoside, N-undecyl-β-D-maltoside, N-dodecyl-β-D-maltoside, digitonin, J1, n-dodecyl-α-maltoside, n-tetradecyl-β-D-maltoside, 1-S-decyl-β-D-thiomaltoside, 1-S-dodecyl-β-D-thiomaltoside, Mega 9 and Mega 10. These nonionic detergents fall into three classes: saccharide, N-oxide and steroid. N-tetradecyl-β-D-maltoside, n-dodecyl-α-maltoside, n-dodecyl-β-maltoside and digitonin resulted in good amplification of a 3 kb target. Many combinations of two positive detergents were tested, two of which performed particularly well in PCR: 0.1% Big Chap and 0.01% Chapso, and 0.05% Big Chap and 0.005% tetradecyl-β-D-maltoside.

Example 9

Tfi Exo−/Exo+ Sensitivity

Figure 3:
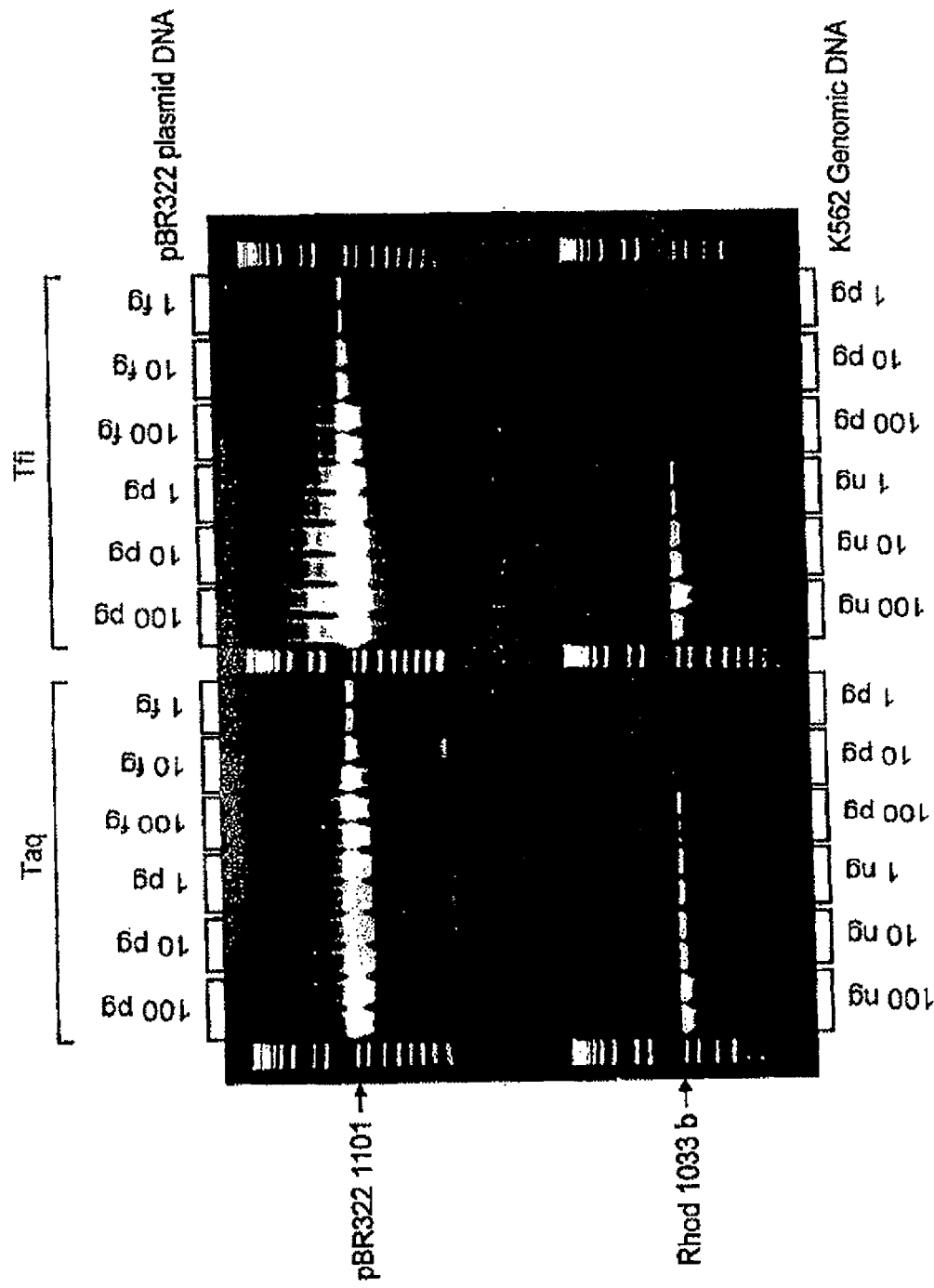
FIG. 3 is a photograph of a gel comparing the sensitivity of Tfi exo-/exo+ blend (7:3 ratio) to Taq DNA polymerase (Invitrogen). Different amounts of plasmid pBR322 or genomic K562 cell DNA fragments of about 1,000 bp were amplified and analyzed by agarose gel electrophoresis.

The sensitivity of a Tfi exo−/exo+ (7:3 ratio) blend was compared to Taq in amplification of both plasmid and genomic DNA. Fragments of about 1,000 bp were amplified using a range of DNA template concentrations. For plasmid DNA, between 1 fg and 100 pg pBR322 were used; and for genomic DNA (Rhod 1033) 1 pg to 100 ng were used. PCR was performed for 35 cycles at 60° C. for 30 sec for annealing, and 72° C. for 1 min 30 s extension. Twenty percent of the final product was analyzed by 0.8% TBE agarose gel electrophoresis for 65 min at a setting of 160 volts. The results (FIG. 3) show that the Tfi blend had greater sensitivity than Taq.

Having now fully described the present invention in some detail by way of illustration and example for purposes of clarity and understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are herein incorporated by reference to the same extent as if each individual publication, patent or patent application was specifically and individually indicated to be incorporated by reference.

What is claimed is:

1. An isolated mutant Tfi DNA polymerase comprising an amino acid sequence having at least 95% identity to SEQ ID NO:2 with a D→A point mutation at amino acid position 144 of SEQ ID NO:2 and an E→D point mutation at position 437 of SEQ ID NO:2.

2. The mutant Tfi DNA polymerase of claim 1, wherein said mutant Tfi DNA polymerase is substantially reduced in 5'-3' exonucleases activity (exo−) as compared to wild type Tfi DNA polymerase.

3. The mutant Tfi DNA polymerase of claim 2, wherein said mutant Tfi DNA polymerase has about or less than 10% of the 5'-3' exonuclease activity as compared to wild type Tfi DNA polymerase.

4. The mutant Tfi DNA polymerase of claim 1, wherein said mutant Tfi DNA polymerase retains at least 5% of its polymerase activity after heating at 95° C. for 30 minutes as compared to wild type Tfi DNA polymerase.

5. The mutant Tfi DNA polymerase of claim 1, wherein said mutant Tfi DNA polymerase has increased thermostability as compared to wild type Tfi DNA polymerase.

6. A composition comprising the mutant Tfi DNA polymerase of claim 1.

7. The composition of claim 6, further comprising a second Tfi DNA polymerase comprising an amino acid sequence having at least 95% identity to SEQ ID NO:2.

8. The composition of claim 7, wherein said second Tfi DNA polymerase comprises the amino acid sequence of SEQ ID NO:2.

9. The composition of claim 7, wherein said second Tfi DNA polymerase is exo+.

10. The composition of claim 7, wherein said composition comprises a ratio of said mutant Tfi DNA polymerase to said second Tfi DNA polymerase selected from the group consisting of about 9:1, about 8:2, about 7:3, about 6:4, about 5:5, about 4:6, about 3:7, about 2:8, and about 1:9.

11. The composition of claim 9, further comprising at least two components selected from the group consisting of a detergent, a buffer salt, at least one deoxynucleoside triphosphate (dNTP), and at least one dideoxynucleoside triphosphate (ddNTP).

12. The composition of claim 9, wherein aid second Tfi DNA polymerase is thermostable.

* * * * *

```
                        SEQUENCE LISTING

<160> NUMBER OF SEQ ID NOS: 12

<210> SEQ ID NO 1
<211> LENGTH: 2508
<212> TYPE: DNA
<213> ORGANISM: Thermus filiformis

<400> SEQUENCE: 1
atgcgaggta tgttaccact gtttgatctg gaagaaccac caaagcgcgt gttattagtg      60
gatggtcacc atttagcata ccgcaccttc tatgcattat ctttaacgac gagccgtggc     120
gaaccggttc aaatggttta tggcttcgca cgctctttat taaaggcgtt aaaggaggac     180
ggccaagcgg ttgtggtggt cttcgatgca aaggcaccta gctttcgtca cgaagcatac     240
gaggcgtata aagcgggccg cgcaccaacc ccagaggact ttccgcggca gctggccctg     300
gtgaaacgct tagtggactt attaggcctg gttcgtttag aggccccagg ttatgaggca     360
gatgatgtcc tgggcacctt agcaaaaaag gccgagcgcg agggcatgga agtgcgtatt     420
ttaaccggtg atcgtgattt tttccaatta ttaagcgaaa aagtgtctgt tttactgccg     480
gacggcacct tagttacccc gaaagatgtg caggaaaaat acggtgttcc gccggagcgt     540
tgggtcgatt ttcgtgcact gacgggtgat cgtagcgata acattccagg tgtcgcaggt     600
attggtgaga aaaccgcgct gcgtttactg gcggaatggg gtagcgtgga aaatttatta     660
aagaatctgg atcgtgttaa gccggatagc gtccgccgca aaattgaagc ccacttagag     720
gatttacgtc tgtctctgga tttagcgcgt atccgtaccg acctgccgct ggaggtcgac     780
ttcaaggcgc tgcgccgccg cacccggat ttagaaggtt tacgcgcctt tctggaagag     840
ttagagttcg gttctctgct gcatgaattt ggtctgttag gtggtgaaaa gccacgcgaa     900
gaagccccgt ggccgccacc ggaagcgcg tttgttggtt ttttactgtc tcgtaaggaa     960
ccgatgtggg cggaattact ggcattagcg gcggcggcag agggtcgtgt gcatcgtgca    1020
```

```
acctctccag tggaggcact ggccgattta aggaagcac  gcggttttct ggcaaaagac      1080
ctggccgttt tagcgctgcg cgaaggcgtt gcgctggatc cgacggatga tccactgctg      1140
gttgcatatt tattagatcc agcgaatacc aatccagaag gtgttgcccg ccgctatggc      1200
ggtgaattta cggaagatgc agcagagcgt gcgttactga cgagcgtct  gtttcagaac      1260
ttatttccgc gtctgtctga aagttactg  tggctgtatc aggaagtgga acgtccactg      1320
tctcgtgtcc tggcgcacat ggaggcacgt ggcgttcgtc tggacgtccc gctgttagag      1380
gcgctgtctt ttgagctcga aaaagagatg gaacgcttag aaggtgaggt cttccgtctg      1440
gcgggtcacc cgtttaatct gaacagccgc gatcagttag agcgcgttct gttcgacgaa      1500
ttaggcctga cgccggtggg ccgtaccgaa aagacgggta agcgctctac cgcccaaggt      1560
gcgctggagg cgctgcgcgg tgcacaccca atcgtggaac tgatcctgca atatcgcgaa      1620
ctgtctaaac tgaagtctac gtacttagac ccattaccac gtttagttca cccgcgcacc      1680
ggccgcctgc acaccgtttt aaccagacg  gcgaccgcaa cgggccgctt aagctcttct      1740
gaccccgaact tacagaatat tccagtgcgt accccactgg gtcagcgcat tcgtaaagca      1800
ttcgtggcgg aagagggctg gctgttatta gccgcagatt attctcagat cgaactgcgc      1860
gtgttagccc atttatctgg cgacgagaat ttaaaacgcg tctttcgtga aggtaaggac      1920
atccataccg agacggcggc ctggatgttc ggtctagatc cggcactggt tgacccaaaa      1980
atgcgccgtg cagcaaagac ggtcaatttc ggcgtgctgt acggtatgtc tgcacaccgc      2040
ttaagccagg aactgggtat tgattacaaa gaggcggagg cattcattga gcgctatttc      2100
cagtctttcc cgaaggtccg cgcctggatc gaacgtacct tagaggaagg tcgtacccgt      2160
ggctatgtgg aaaccctgtt tggccgccgt cgttatgttc cagatctggc cagccgtgtg      2220
cgctctgtcc gcgaggcagc agagcgtatg gcatttaata tgccagtcca aggtacggcc      2280
gcagatttaa tgaagatcgc tatggtgaag ttattcccac gcttaaaacc actgggcgcc      2340
cacctgctgt acaagttca  tgatgagctt gtgctggagg ttccagagga tcgcgccgag      2400
gaagcaaagg ccctggttaa ggaagtgatg gagaatacgt acccgctgga tgttccgctg      2460
gaagttgaag ttggtgtcgg tcgagattgg ctcgaggcaa agggcgac                   2508
```

<210> SEQ ID NO 2
<211> LENGTH: 836
<212> TYPE: PRT
<213> ORGANISM: Thermus filiformis

<400> SEQUENCE: 2

```
Met Arg Gly Met Leu Pro Leu Phe Asp Leu Glu Glu Pro Pro Lys Arg
1               5                   10                  15

Val Leu Leu Val Asp Gly His His Leu Ala Tyr Arg Thr Phe Tyr Ala
            20                  25                  30

Leu Ser Leu Thr Thr Ser Arg Gly Glu Pro Val Gln Met Val Tyr Gly
        35                  40                  45

Phe Ala Arg Ser Leu Leu Lys Ala Leu Lys Glu Asp Gly Gln Ala Val
    50                  55                  60

Val Val Val Phe Asp Ala Lys Ala Pro Ser Phe Arg His Glu Ala Tyr
65                  70                  75                  80

Glu Ala Tyr Lys Ala Gly Arg Ala Pro Thr Pro Glu Asp Phe Pro Arg
                85                  90                  95

Gln Leu Ala Leu Val Lys Arg Leu Val Asp Leu Leu Gly Leu Val Arg
            100                 105                 110
```

```
Leu Glu Ala Pro Gly Tyr Ala Asp Asp Val Leu Gly Thr Leu Ala
        115                 120                 125

Lys Lys Ala Glu Arg Glu Gly Met Glu Val Arg Ile Leu Thr Gly Asp
    130                 135                 140

Arg Asp Phe Phe Gln Leu Leu Ser Glu Lys Val Ser Val Leu Leu Pro
145                 150                 155                 160

Asp Gly Thr Leu Val Thr Pro Lys Asp Val Gln Glu Lys Tyr Gly Val
                165                 170                 175

Pro Pro Glu Arg Trp Val Asp Phe Arg Ala Leu Thr Gly Asp Arg Ser
            180                 185                 190

Asp Asn Ile Pro Gly Val Ala Gly Ile Gly Glu Lys Thr Ala Leu Arg
            195                 200                 205

Leu Leu Ala Glu Trp Gly Ser Val Glu Asn Leu Leu Lys Asn Leu Asp
        210                 215                 220

Arg Val Lys Pro Asp Ser Val Arg Arg Lys Ile Glu Ala His Leu Glu
225                 230                 235                 240

Asp Leu Arg Leu Ser Leu Asp Leu Ala Arg Ile Arg Thr Asp Leu Pro
                245                 250                 255

Leu Glu Val Asp Phe Lys Ala Leu Arg Arg Arg Thr Pro Asp Leu Glu
            260                 265                 270

Gly Leu Arg Ala Phe Leu Glu Glu Leu Glu Phe Gly Ser Leu Leu His
        275                 280                 285

Glu Phe Gly Leu Leu Gly Gly Glu Lys Pro Arg Glu Ala Pro Trp
    290                 295                 300

Pro Pro Pro Glu Gly Ala Phe Val Gly Phe Leu Ser Arg Lys Glu
305                 310                 315                 320

Pro Met Trp Ala Glu Leu Leu Ala Leu Ala Ala Ala Glu Gly Arg
                325                 330                 335

Val His Arg Ala Thr Ser Pro Val Glu Ala Leu Ala Asp Leu Lys Glu
            340                 345                 350

Ala Arg Gly Phe Leu Ala Lys Asp Leu Ala Val Leu Ala Leu Arg Glu
        355                 360                 365

Gly Val Ala Leu Asp Pro Thr Asp Pro Leu Leu Val Ala Tyr Leu
    370                 375                 380

Leu Asp Pro Ala Asn Thr Asn Pro Glu Gly Val Ala Arg Arg Tyr Gly
385                 390                 395                 400

Gly Glu Phe Thr Glu Asp Ala Ala Glu Arg Ala Leu Leu Ser Glu Arg
                405                 410                 415

Leu Phe Gln Asn Leu Phe Pro Arg Leu Ser Glu Lys Leu Leu Trp Leu
            420                 425                 430

Tyr Gln Glu Val Glu Arg Pro Leu Ser Arg Val Leu Ala His Met Glu
        435                 440                 445

Ala Arg Gly Val Arg Leu Asp Val Pro Leu Leu Glu Ala Leu Ser Phe
    450                 455                 460

Glu Leu Glu Lys Glu Met Glu Arg Leu Glu Gly Val Phe Arg Leu
465                 470                 475                 480

Ala Gly His Pro Phe Asn Leu Asn Ser Arg Asp Gln Leu Glu Arg Val
                485                 490                 495

Leu Phe Asp Glu Leu Gly Leu Thr Pro Val Gly Arg Thr Glu Lys Thr
            500                 505                 510

Gly Lys Arg Ser Thr Ala Gln Gly Ala Leu Glu Ala Leu Arg Gly Ala
        515                 520                 525
```

```
His Pro Ile Val Glu Leu Ile Leu Gln Tyr Arg Glu Leu Ser Lys Leu
    530                 535                 540
Lys Ser Thr Tyr Leu Asp Pro Leu Pro Arg Leu Val His Pro Arg Thr
545                 550                 555                 560
Gly Arg Leu His Thr Arg Phe Asn Gln Thr Ala Thr Ala Thr Gly Arg
                565                 570                 575
Leu Ser Ser Ser Asp Pro Asn Leu Gln Asn Ile Pro Val Arg Thr Pro
            580                 585                 590
Leu Gly Gln Arg Ile Arg Lys Ala Phe Val Ala Glu Gly Trp Leu
        595                 600                 605
Leu Leu Ala Ala Asp Tyr Ser Gln Ile Glu Leu Arg Val Leu Ala His
    610                 615                 620
Leu Ser Gly Asp Glu Asn Leu Lys Arg Val Phe Arg Glu Gly Lys Asp
625                 630                 635                 640
Ile His Thr Glu Thr Ala Ala Trp Met Phe Gly Leu Asp Pro Ala Leu
                645                 650                 655
Val Asp Pro Lys Met Arg Arg Ala Ala Lys Thr Val Asn Phe Gly Val
            660                 665                 670
Leu Tyr Gly Met Ser Ala His Arg Leu Ser Gln Glu Leu Gly Ile Asp
        675                 680                 685
Tyr Lys Glu Ala Glu Ala Phe Ile Glu Arg Tyr Phe Gln Ser Phe Pro
    690                 695                 700
Lys Val Arg Ala Trp Ile Glu Arg Thr Leu Glu Glu Gly Arg Thr Arg
705                 710                 715                 720
Gly Tyr Val Glu Thr Leu Phe Gly Arg Arg Tyr Val Pro Asp Leu
                725                 730                 735
Ala Ser Arg Val Arg Ser Val Arg Glu Ala Ala Glu Arg Met Ala Phe
            740                 745                 750
Asn Met Pro Val Gln Gly Thr Ala Ala Asp Leu Met Lys Ile Ala Met
        755                 760                 765
Val Lys Leu Phe Pro Arg Leu Lys Pro Leu Gly Ala His Leu Leu Leu
    770                 775                 780
Gln Val His Asp Glu Leu Val Leu Glu Val Pro Glu Asp Arg Ala Glu
785                 790                 795                 800
Glu Ala Lys Ala Leu Val Lys Glu Val Met Glu Asn Thr Tyr Pro Leu
                805                 810                 815
Asp Val Pro Leu Glu Val Glu Val Gly Val Gly Arg Asp Trp Leu Glu
            820                 825                 830
Ala Lys Gly Asp
        835

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaaactgcca tgctcagaga                                              20

<210> SEQ ID NO 4
<211> LENGTH: 20
<212> TYPE: DNA
<213> ORGANISM: Artificial Sequence
<220> FEATURE:
```

-continued

<223> OTHER INFORMATION: Description of Artificial Sequence: Synthetic
     primer

<400> SEQUENCE: 4
atttatttgt gagggacgc                                                    20

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 5
cagccccttc gagtacccac agt                                               23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 6
tgctcaccac cccatgaagt tt                                                22

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 7
cctggcaccc agcacaat                                                     18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 8
gggccggact cgtcatac                                                     18

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 9
agccgccgat ccacacgagt                                                   20

<210> SEQ ID NO 10
<211> LENGTH: 832
<212> TYPE: PRT
<213> ORGANISM: Thermus aquaticus

<400> SEQUENCE: 10

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
        130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415
```

```
Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
        450                 455                 460

Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830
```

```
<210> SEQ ID NO 11
<211> LENGTH: 5
<212> TYPE: PRT
<213> ORGANISM: Thermus filiformis

<400> SEQUENCE: 11

Thr Gly Ala Arg Asp
1               5

<210> SEQ ID NO 12
<211> LENGTH: 5
<212> TYPE: PRT
<213> ORGANISM: Thermus filiformis

<400> SEQUENCE: 12

Glu Val Asp Arg Pro
1               5
```